(12) United States Patent
Miranda et al.

(10) Patent No.: US 12,128,145 B2
(45) Date of Patent: Oct. 29, 2024

(54) DECONTAMINATION ROBOT WITH SWERVE DRIVE AND SCISSOR LIFT

(71) Applicant: Cardinal Gibbons High School, Raleigh, NC (US)

(72) Inventors: Benjamin James Miranda, Durham, NC (US); Thomas Ryan Michael Greene, Raleigh, NC (US); Ethan James Dominic, Cary, NC (US); Charles Joseph Kilani, Raleigh, NC (US); William Michael Meyers, Chapel Hill, NC (US); Daniel Thomas Mahon, Cary, NC (US); John Michael Gebhardt, Cary, NC (US); Joseph Michael Biersack, Morrisville, NC (US); Ilam Maya, Raleigh, NC (US); Gillian Nicole Kearney, Raleigh, NC (US); Brett Richard Gallagher, Raleigh, NC (US); Brigitte Noelle Gallagher, Raleigh, NC (US); Ayda Rose Suing, Raleigh, NC (US); Nicole Carol Allen, Raleigh, NC (US); Cassian Farias Kraus, Apex, NC (US); Zachary Clayton Naylor, Raleigh, NC (US)

(73) Assignee: Cardinal Gibbons High School, Raleigh, NC (US)

( * ) Notice: Subject to any disclaimer, the term of this patent is extended or adjusted under 35 U.S.C. 154(b) by 727 days.

(21) Appl. No.: 17/170,570

(22) Filed: Feb. 8, 2021

(65) Prior Publication Data

US 2021/0154343 A1    May 27, 2021

(51) Int. Cl.
*A61L 2/10*    (2006.01)
*A61L 2/24*    (2006.01)
(Continued)

(52) U.S. Cl.
CPC .............. *A61L 2/10* (2013.01); *A61L 2/24* (2013.01); *A61L 2/26* (2013.01); *B66F 3/22* (2013.01);
(Continued)

(58) Field of Classification Search
CPC ......... A61L 2/10; A61L 2202/122; A61L 2/24
See application file for complete search history.

(56) References Cited

U.S. PATENT DOCUMENTS 8,754,385 B1 *  6/2014  Gutman ............... A01N 1/0273
                                                250/455.11
8,794,386 B2    8/2014  Keeling et al.
(Continued)

FOREIGN PATENT DOCUMENTS

AU    2020102710 A4 * 12/2020
EP        2801375 A1 * 11/2014 ............... A61L 2/10
(Continued)

OTHER PUBLICATIONS

"A pantograph mirror", Jan. 6, 2010, Wikipedia, https://en.wikipedia.org/wiki/Scissors_mechanism#/media/File: Pantograph_Mirror.gif (Year: 2010).*

(Continued)

*Primary Examiner* — Kevin Joyner
*Assistant Examiner* — Changru Chen
(74) *Attorney, Agent, or Firm* — Haynes and Boone, LLP

(57) ABSTRACT

Disclosed is a decontamination robot. The robot includes a decontamination box including at least two arrays of ultraviolet LEDs, the two arrays arranged to irradiate an object placed inside the decontamination box from at least two independent directions, the decontamination box further including an interior surface with at least 90% reflectivity of ultraviolet light. The robot also includes a drivetrain including four swerve-drive units, each swerve-drive unit capable of rotating a wheel on an axis of the wheel and capable of (Continued)

orienting the wheel in a plane defined by the axes of the four wheels of the four swerve-drive units, whereby the four swerve-drive units coordinate to generate translational motion of the decontamination robot on a working surface. The robot also includes a scissor lift capable of raising the decontamination box from a first position to a second position, wherein the scissor lift comprises a plurality of bars connected by a plurality of joints such that the plurality of bars form a series of crosses, and a top plate attached to a top of the decontamination box.

10 Claims, 18 Drawing Sheets

(51) Int. Cl.
*A61L 2/26* (2006.01)
*B66F 3/22* (2006.01)

(52) U.S. Cl.
CPC ...... *A61L 2202/11* (2013.01); *A61L 2202/122* (2013.01); *A61L 2202/14* (2013.01)

(56) References Cited

U.S. PATENT DOCUMENTS

| | | | |
|---|---|---|---|
| 9,211,922 B2 | 12/2015 | Keeling et al. | |
| 9,864,369 B2 | 1/2018 | Gravel et al. | |
| 10,384,338 B2 | 8/2019 | Greene et al. | |
| 10,647,351 B2 | 5/2020 | Bain et al. | |
| 2015/0314026 A1* | 11/2015 | Mauzerall | A61B 50/33 96/417 |
| 2017/0035923 A1* | 2/2017 | Yanke | A61L 2/0088 |
| 2017/0112954 A1* | 4/2017 | Dayton | A61L 9/20 |
| 2020/0111333 A1* | 4/2020 | Liivik | G09F 27/00 |
| 2021/0078183 A1 | 3/2021 | Greene et al. | |

FOREIGN PATENT DOCUMENTS

| | | | | | |
|---|---|---|---|---|---|
| JP | 2019524215 A | * | 9/2019 | | A61L 2/10 |
| KR | 101742489 B1 | * | 6/2017 | | A61L 2/24 |
| WO | WO-2010127296 A2 | * | 11/2010 | | A61L 2/04 |
| WO | 102017209966 A1 | * | 12/2018 | | A61L 2/26 |
| WO | WO-2019246394 A1 | * | 12/2019 | | A61L 2/10 |

OTHER PUBLICATIONS

Back to the Drawing Board, "FTC Team 5795: Robot Reveal", Mar. 12, 2017, Youtube, https://www.youtube.com/watch?v=mg-tpWHZTtw (Year: 2017).*
"Crab/Swerve Drive", Jun. 1, 2019, Robot Patterns, https://www.robotpatterns.com/mechanical/drivetrain/crab-swerve-drive (Year: 2019).*
Jan, "Continuous-rotation servos and multi-turn servos", Jul. 26, 2011, Pololu, https://www.pololu.com/blog/24/continuous-rotation-servos-and-multi-turn-servos (Year: 2011).*
"Swerve & Steer", Jan. 2020, Andymark, https://www.andymark.com/products/swerve-and-steer (Year: 2020).*
J Wilder, "Running Swerve Drive", Jan. 21, 2020, Youtube, https://www.youtube.com/watch?v=l3jKAWxHDOQ (Year: 2020).*
FTC Engineering, "The FTC Control System", Jun. 27, 2019, Github, https://github.com/ftctechnh/ftc_app/wiki/The-FTC-Control-System (Year: 2019).*
"Gyro vs. Encoders for Driving Straight", Oct. 2016, Chief Delphi, https://www.chiefdelphi.com/t/gyro-vs-encoders-for-driving-straight/153650 (Year: 2016).*
KR 101742489 B1_translation (Year: 2017).*
JP 2019524215 A _translation (Year: 2019).*
DE 102017209966 A1_translation (Year: 2018).*
Bain et al., "Robotic Platform With Wheeled Legs and Virtual Differential Transmission" U.S. Appl. No. 62/431,152, filed Dec. 7, 2016, Expired, 32 pages.

* cited by examiner

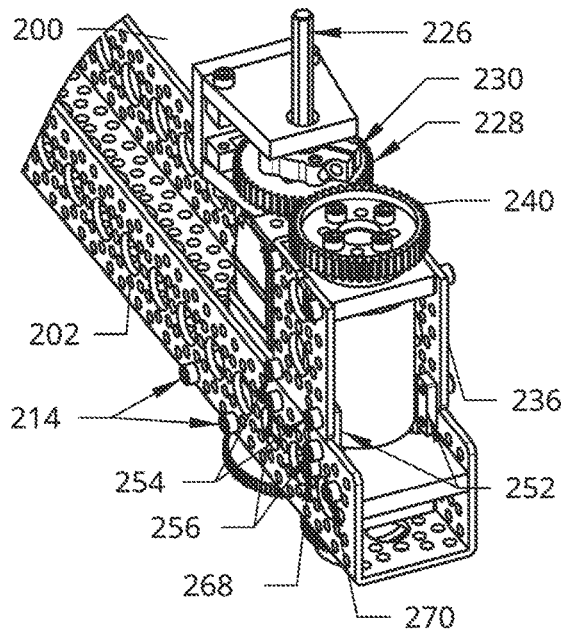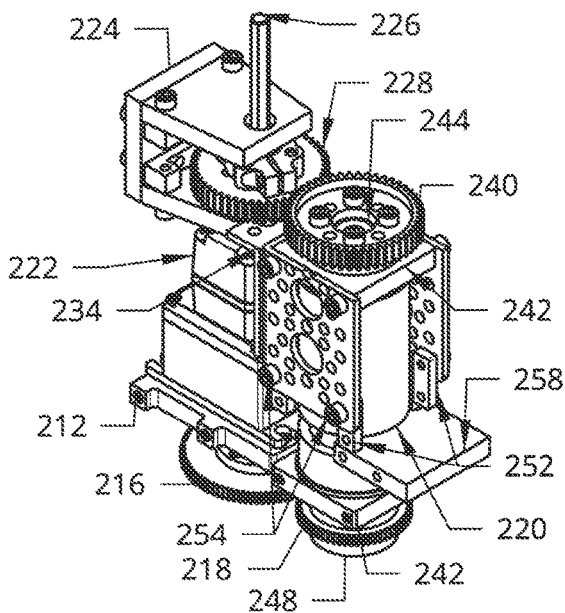
Figure 2a
Figure 2b
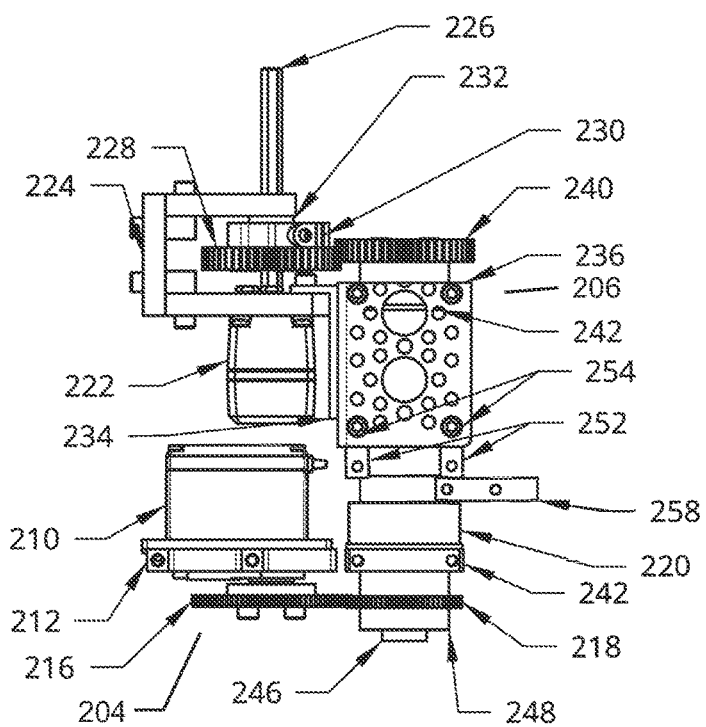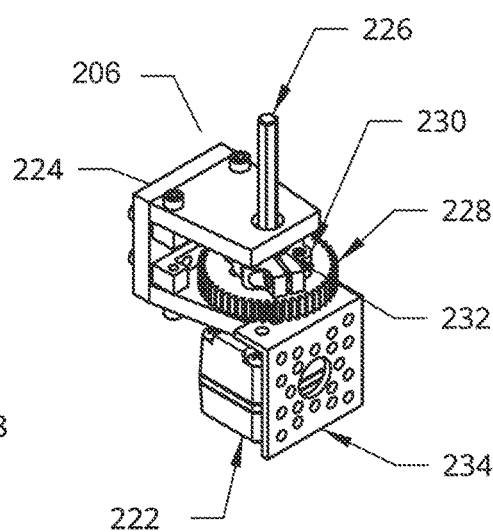
Figure 2c
Figure 2d

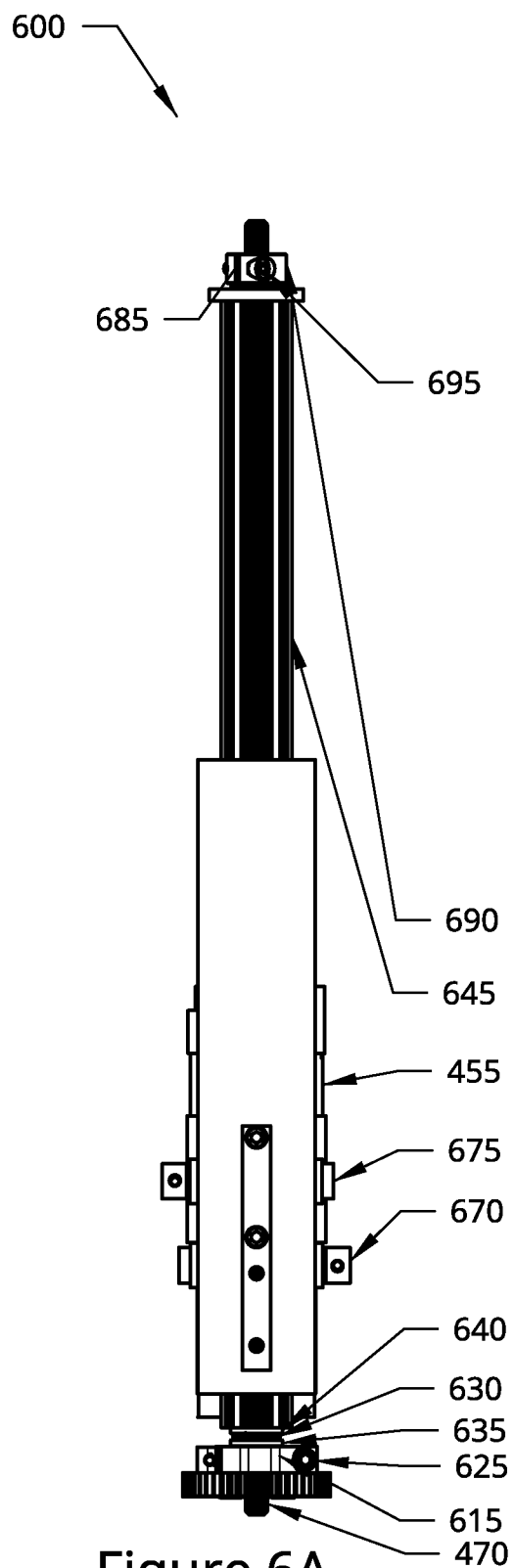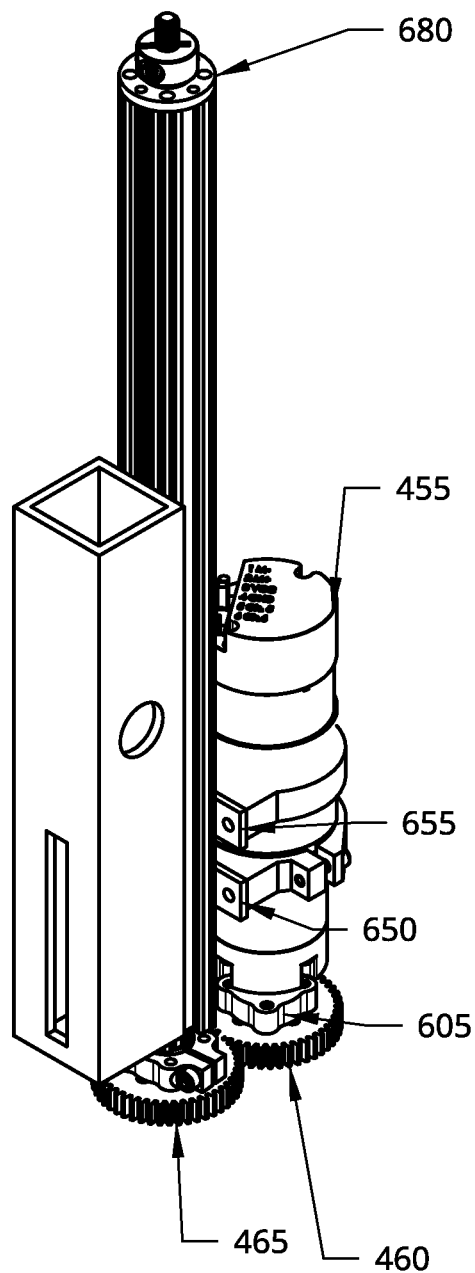
Figure 6A
Figure 6B

DECONTAMINATION ROBOT WITH SWERVE DRIVE AND SCISSOR LIFT

TECHNICAL FIELD

The subject matter described herein relates to a decontamination robot for retrieving, carrying, and decontaminating small objects. This robot has particular but not exclusive utility for health care, manufacturing, and space exploration.

BACKGROUND

Infectious pathogens may exist in hospital settings on items such as personal protective equipment (PPE), like masks, respirators, and personal hoods. Conventional decontamination procedures, such as the use of alcohol and bleaches, cannot reliably clean these one-time-use items, so the items are typically thrown away after twenty-four hours based on current protocols. The decontamination process also often requires physical contact with the item to be decontaminated, which increases the risk of cross-contamination. To save time and reduce the risk of cross-contamination, a robot is needed to transport small items or metal objects from one place to another and decontaminate the items in the process. A robot is needed to migrate between areas of a space that requires decontamination, such as a hospital. A robot could be deployed in an Intensive Care Unit (ICU) or Emergency Room. A robot such as this would be helpful during the COVID-19 pandemic. Accordingly, long-felt need exists for robots that address the forgoing and other concerns.

The information included in this Background section of the specification, including any references cited herein and any description or discussion thereof, is included for technical reference purposes only and is not to be regarded as subject matter by which the scope of the disclosure is to be bound.

SUMMARY

Disclosed is a decontamination robot which may be equipped with a swerve drive and a scissor lift. The technologies and techniques disclosed herein may have particular, but not exclusive, utility for health care, manufacturing, and space exploration. A decontamination robot incorporating some of the disclosed concepts may include a decontamination box including at least two arrays of ultraviolet LEDs, the two arrays arranged to irradiate an object placed inside the decontamination box from at least two independent directions, the decontamination box further including an interior surface providing at least 90% reflectivity of ultraviolet light; a drivetrain including a frame and four swerve-drive units connected by the frame, each swerve-drive unit including a wheel and capable of rotating the wheel on a first axis, where the four swerve-drive units are arranged such that the first axes of the four wheels are substantially coplanar and define a plane that is substantially parallel to a working surface, and where each swerve-drive unit is capable of rotating the wheel on a second axis, where the second axis is perpendicular to the plane; the drivetrain further including a processor to provide control signals to the four swerve-drive units to coordinate the rotation of the wheels about their first and second axes to generate translational motion of the decontamination robot on the working surface; a scissor lift capable of raising the decontamination box from a first position to a second position, wherein the scissor lift comprises a plurality of bars connected by a plurality of joints such that the plurality of bars form a series of crosses; and a top plate attached to a top of the decontamination box. Other embodiments of this aspect include corresponding methods, computer systems, apparatus, and computer programs recorded on one or more computer storage devices, each configured to perform the actions of the methods.

Implementations may include one or more of the following features. A decontamination robot, where the decontamination box includes at least one plate that is substantially transparent to ultraviolet radiation and configured to hold an item for decontamination, and where each array of LED lights is mounted on a circuit board. A decontamination robot, where the scissor lift is connected to a bottom set of carriages attached to a bottom sliding mechanism and a top set of carriages attached to a top sliding mechanism, the bottom sliding mechanism being connected to a horizontal bar. A decontamination robot, further including a piston configured to exert upward force on the scissor lift such that the scissor lift extends. A decontamination robot, where each swerve-drive unit includes: a steering unit configured to rotate the wheel about the second axis, where the steering unit includes a steering column, a potentiometer arranged to provide a signal corresponding to a rotational angle of the steering column, a servo configured to rotate the steering column, and a hard stop plate for protecting the potentiometer and servo from over-rotation; and a drive unit configured to rotate the wheel about the first axis, wherein the drive unit comprises a gear motor configured to selectively rotate the wheel about the first axis in a clockwise and counter-clockwise motion. A decontamination robot, further including at least one side plate attached to the frame of the drivetrain and extending down toward the floor such that the side plate covers a space between two of the swerve-drive units, the side plate configured to prevent debris from becoming trapped under the frame of the drivetrain, thereby protecting an undercarriage area of the decontamination robot from damage. A decontamination robot, further including a camera capable of scanning a QR code. A decontamination robot, further including a flag configured to extend, calling attention to the decontamination robot. A decontamination robot, where the processor is a smartphone. A decontamination robot, where the processor keeps track of an orientation of the decontamination robot by integrating an inertial measurement unit gyroscope, and wherein the processor keeps track of a position of the decontamination robot by integrating traction drivetrain rotation encoders, and wherein the processor detects a presence of a nearby object based on an input from a camera. A decontamination robot, further including a trailer dragger configured to selectively engage with a target object on the working surface. A decontamination robot, further including a crane configured to extend from the top plate and a claw attached to the crane configured to selectively engage with one or more target objects above the working surface. This Summary is provided to introduce a selection of concepts in a simplified form that are further described below in the Detailed Description. This Summary is not intended to identify key features or essential features of the claimed subject matter, nor is it intended to limit the scope of the claimed subject matter. A more extensive presentation of features, details, utilities, and advantages of the claimed subject matter is provided in the following written description of various embodiments of the disclosure and illustrated in the accompanying drawings.

BRIEF DESCRIPTION OF THE DRAWINGS

Illustrative embodiments of the present disclosure will be described with reference to the accompanying drawings, of which:

FIG. 2a, FIG. 2b, FIG. 2c, FIG. 2d, FIG. 2e, and FIG. 2f show views of a swerve-drive unit in accordance with at least one embodiment of the present disclosure.

FIG. 6a and FIG. 6b show a piston mechanism in accordance with at least one embodiment of the present disclosure.

DETAILED DESCRIPTION

Figure 1:
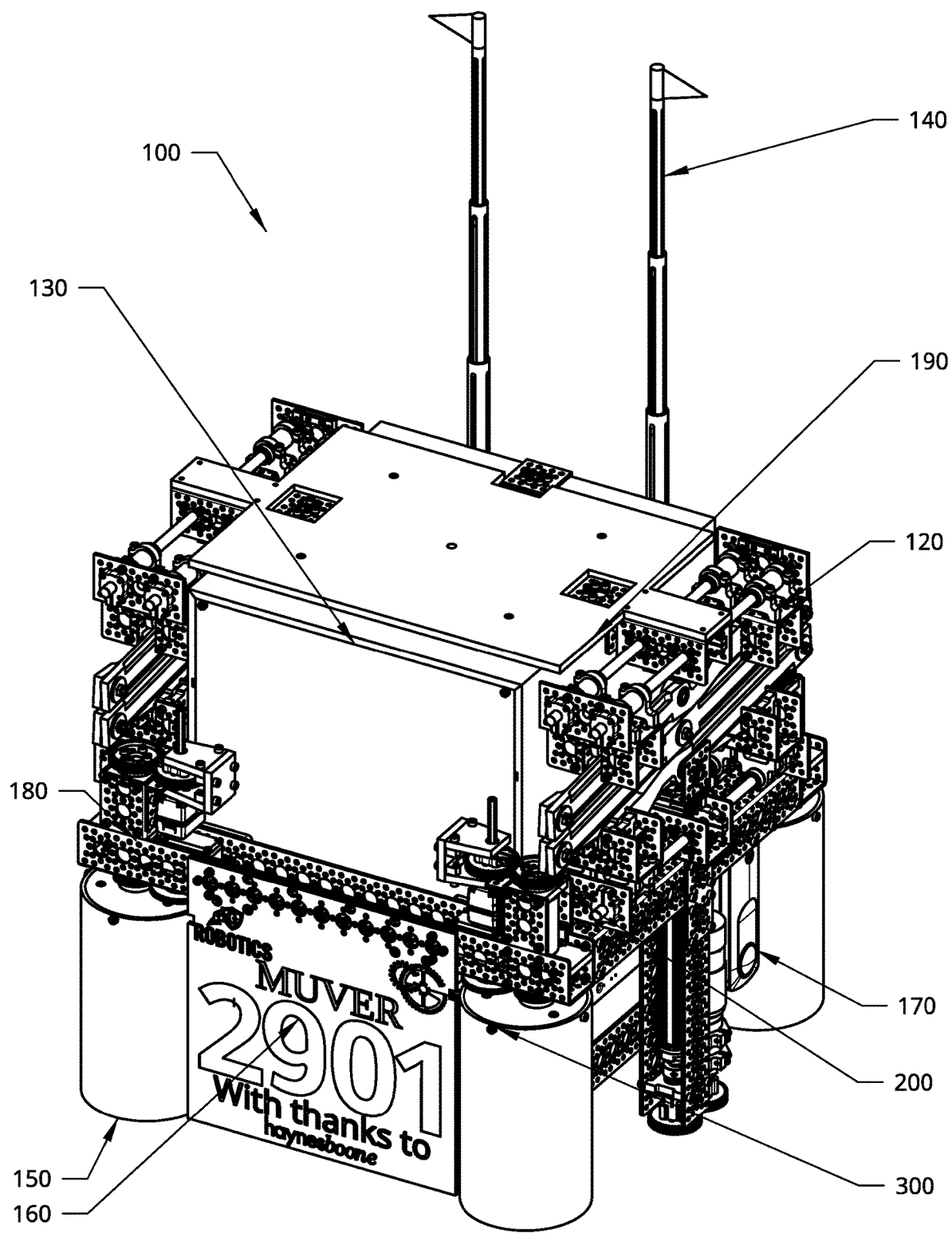
FIG. 1 is a perspective view of a robot in accordance with at least one embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

In accordance with at least one embodiment of the present disclosure, a decontamination robot with swerve drive and scissor lift is provided which is configured to raise for accepting objects, lower to decontaminate and transport objects, raise for delivering decontaminated objects to the same or different location, and grab and transport objects.

These descriptions are provided for exemplary purposes only and should not be considered to limit the scope of the decontamination robot with swerve drive and scissor lift. Certain features may be added, removed, or modified without departing from the spirit of the claimed subject matter.

FIG. 1 is a perspective view of a robot 100 with drivetrain, scissor lift, and decontamination box in accordance with at least one embodiment of the present disclosure. The robot 100 includes a drivetrain, a scissor lift 120, a decontamination box 130, and various safety features. The robot 100 may include a trailer dragging system 1000 and a crane 1100, but for visual clarity, the trailer dragging system 1000 and the crane 1100 are not shown in this view.

The drivetrain includes a frame 180 and four swerve-drive units 110. The frame 180 holds together the four swerve-drive units 110. Each swerve-drive unit 110 includes a steering section 200 and a drive section 300. The drivetrain enables the robot 100 to move precisely and provides good maneuverability so the robot 100 can move around in tight spaces, as may be found in some hospitals. The scissor lift 120 raises and lowers the decontamination box 130 for loading and retrieval of materials. The scissors lift 120 extends the decontamination box 130 up to a useful height for human interaction. The decontamination box 130 decontaminates items placed inside the decontamination box 130. In one exemplary process, decontamination may be achieved by using irradiation via ultraviolet LEDs emitting light that is reflected by a Teflon layer on the interior of the decontamination box 130. The decontamination box 130 has a mini scissor lift (not pictured) attached to the back, which extends as the scissor lift 120 extends, to carry the wiring for powering the lights in the decontamination box 130. On top of the decontamination box 130 is a top plate 190.

The safety features may include a flag system 140, swerve guards 150, a side plate 160, and a camera 170. The flag system 140 extends to alert people of the robot 100's presence. The flag system 140 may reach eye level and may sway slightly to attract attention. The swerve guards 150 may each be a 3D printed cylinder that surrounds the drive section 300 of a swerve-drive unit 110. The swerve guard 150 protects the drive section 300 from harm and prevents foreign objects from getting caught in the drive section 300. The side plate 160 prevents foreign objects from getting caught underneath the robot 100. The side plate 160 protects the components of the robot 100 from being damaged by an object passing underneath the frame 180 of the drivetrain. The side plate 160 may be attached to the frame 180 of the drivetrain and extend down toward the floor such that the side plate 160 covers the space between two swerve-drive units 110. The camera 170, together with associated intelligent processing capabilities described below, allows the robot 100 to identify and avoid obstacles. The camera 170 may provide full 360-degree vision. In one embodiment, the camera 170 may be a Ricoh Theta M15.

The robot 100 may be summoned to a specific location by input in a phone application. The input may be generated by a user of the phone application or may be generated by another smartphone and received by the phone application over a direction connection WIFI signal. The robot 100 may use robot-relative control, in which input of a forward direction on the controls results in the robot 100 moving toward the absolute position of the forward direction, regardless of the direction that the robot 100 is currently facing. The robot 100 may also use drive-relative control, in which input of a forward direction on the controls results in the robot 100 moving forward in space toward the direction it is currently facing.

The robot 100 may be controlled via an autonomous mode program, which includes executable code to control operation of the swerve-drive units 110. In an example, the robot may use an on-board smartphone as a processor for executing instructions to achieve autonomous mode control.

An on-board smartphone or other component may include an inertial measurement unit (IMU) gyroscope from which position information, orientation information, or both, may be derived. In an example, the IMU gyroscope has a scale from −180 to 180 degrees, and to ensure that the robot turns a precisely desired amount, the robot's turning speed may be reduced as it approaches a desired angle. For example, the turning speed may be controlled in direct proportion to the turning distance left to the desired angle. With encoders on the robot 100 that monitor the distance the robot 100 has traveled, the processor keeps track of position. The processor also may include object detection using, for example, the machine learning programs Vuforia and TensorFlow. In an example, the machine learning programs will ascertain the distance and position of an object relative to the camera 170, and the processor will consider the object information in combination with the current position of the robot 100 and a preplanned route of the robot 100 to ascertain whether the detected object is in the path of the robot 100. The robot 100 may also detect objects using a distance sensor instead of the camera 170. Regardless, the robot 100 may change directions or stop if the detected object is within a specified range of the robot 100.

Before continuing, it should be noted that the examples described above are provided for purposes of illustration and are not intended to be limiting. Other devices and/or device configurations may be utilized to carry out the operations described herein.

Figure 2E:
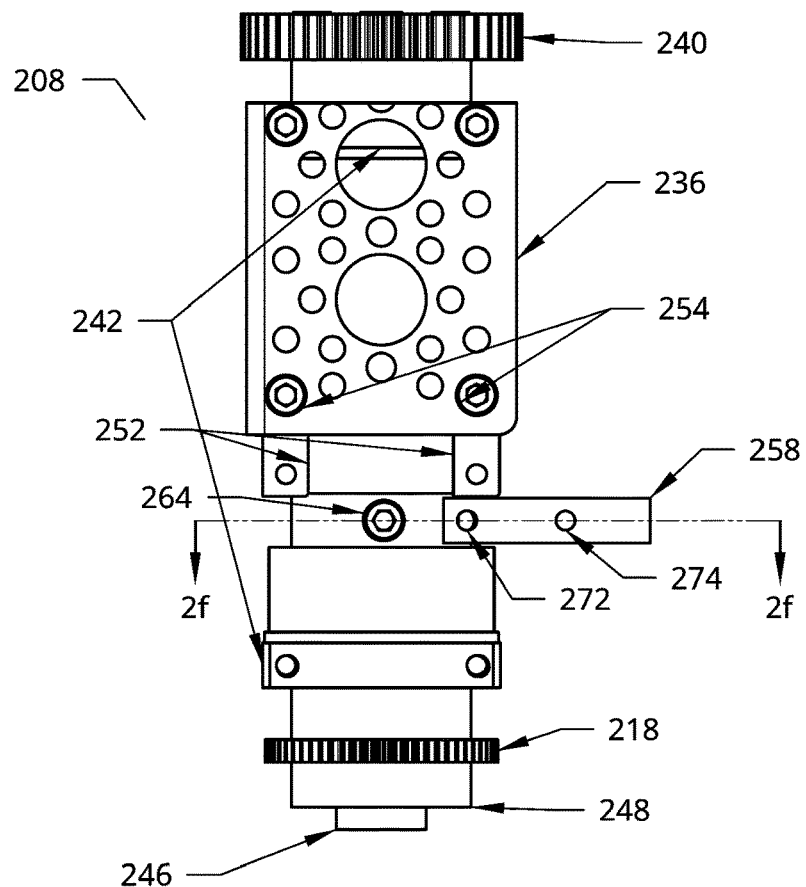
Figure 2F:
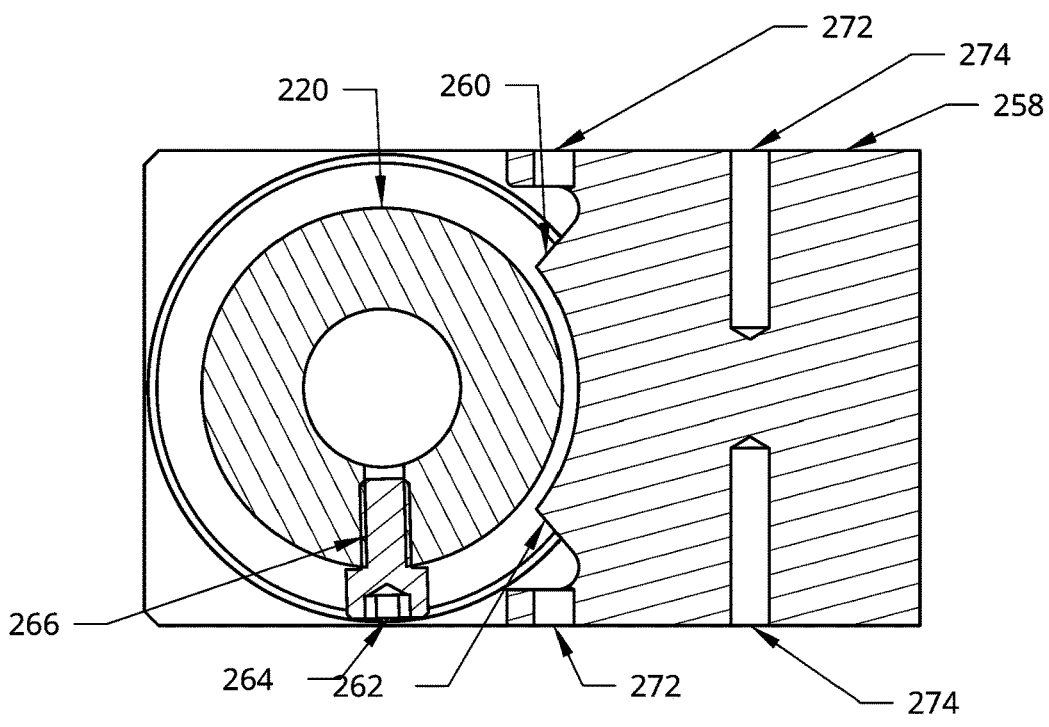

FIG. 2a, FIG. 2b, FIG. 2c, FIG. 2d, FIG. 2e, and FIG. 2f show views of the steering section 200 of a swerve-drive unit 110 in accordance with at least one embodiment of the present disclosure. In FIG. 2a, a perspective view of the steering section 200 is shown with a frame bar 202, which is a portion of frame 180 and connects the steering section 200 to the rest of the swerve-drive units 110. In FIG. 2b, a perspective view of the steering section 200 is shown without the frame bar 202. In FIG. 2c, a front view of the steering section 200 is shown, including a servo section 204, a potentiometer section 206, and a steering column section 208. In FIG. 2d, a perspective view of the potentiometer section 206 is shown. In FIG. 2e, a front view of the steering column section 208 is shown. In FIG. 2f, a sectional view of FIG. 2e along the 2f line is shown.

The servo section 204 includes a servo 210. The servo 210 is held in place by a servo mount 212. The servo mount 212 is affixed to the frame bar 202 via a set of screws 214 that go through the sides of the frame bar 202 and into the threaded holes in the sides of the servo mount 212. A steering gear 216 is attached to the bottom of the servo mount 212. The servo mount 212 is positioned such that steering gear 216 interlocks with another steering gear 218 attached to a steering column 220 in the steering column section 208. Steering gear 216 is larger than steering gear 218, so that the servo 210 can turn faster and farther than the steering column 220.

The potentiometer section 206 includes a potentiometer 222. The potentiometer 222 is held in place by a potentiometer mount 224. The potentiometer mount 224 also holds in place a potentiometer shaft 226, which passes into the center of the potentiometer 222. The potentiometer shaft 226 is connected to a top gear 228 by a hub 230. A bushing 232 sits between the hub 230 and the top side of the potentiometer mount 224. Therefore, the side and top of the potentiometer mount 224 ensure that bushing 232 and top gear 228 remain on potentiometer shaft 226 and that potentiometer shaft 226 remains connected to potentiometer 222.

A bracket 234 connects an extension bar 236 to the bottom plate of the potentiometer mount 224. The bracket 234 allows enough room for the heads of potentiometer screws 238 to go through the bottom plate of the potentiometer mount 224, and into the potentiometer 222. The bracket 234 also determines the distance of the potentiometer 222 and the potentiometer shaft 226 from the steering column 220. The distance is such that the top gear 228 interlocks with a top gear 240 attached to the steering column 220.

The potentiometer 222 measures the motion of the steering column 220. As the steering column 220 rotates, top gear 240 turns, which causes top gear 228 to turn. The rotating motion passes from gear 228, through hub 230, and into potentiometer shaft 226. The potentiometer 222 measures the motion of potentiometer shaft 226. The potentiometer 222 measures the motion of the steering column 220 accurately by measuring the motion of the potentiometer shaft 226 because top gear 228 and top gear 240 have a 1:1 gear ratio, such that the motion of the steering column 220 is passed on to the potentiometer 222 without any multiplier. Therefore, the potentiometer 222 can directly and accurately measure the motion and position of the steering column 220.

The steering column section 208 includes the steering column 220. The steering column 220 rests on a pillow block 242 below. The bottom pillow block 242 prevents the steering column 220 from tilting or becoming misaligned. A second pillow block 242 above the steering column 220 holds the weight of the robot 100 such that the upper pillow block 242 pushes down on the steering column 220. The pillow blocks 242 are positioned such that the steering column 220 cannot move up or down but is still able to rotate in place. The steering column 220 has a through hole 244 at its center. The through hole 244 allows wires to pass from down below in the drive section 300 of the swerve-drive unit 110 up into the steering section 200 of the swerve-drive unit 110. At the bottom end of the steering column 220, the circumference of the steering column 220 decreases, and the wall gets particularly thin. This is called the shoulder 246. The shoulder 246 fits into the top hole 305 of the drive section 300 to ensure that the drive section 300 does not twist away from the steering section 200 and to maintain alignment of the through hole 244 of the steering column 220 with the top hole 305 of the drive section 300.

A hub spacer 248 abuts the bottom side of steering gear 218, maintaining space between steering gear 218 and the drive section 300. Hub spacer 248 ensures that steering gear 218 remains aligned and interlocked with steering gear 216. Hub spacer 248 also ensures that the drive section 300 does not interfere with the interlocking of steering gear 216 and steering gear 218.

The extension bar 236 elevates the top pillow block 242 so that any movement due to manufacturing tolerances has a minimal effect on the angle of the steering column 220. The extension bar 236 is attached to the frame bar 202 via four attachment plates 252. The attachment plates 252 connect the extension bar 236 to the frame bar 202 without interfering with the steering column 220. To achieve this, a set of screws 254 go through the sides of the extension bar 236 and into the threaded holes of the attachment plates 252, securing the attachment plates 252 to the extension bar 236. Below the set of screws 254 is another set of screws 256 that go through the frame bar 202 and into the threaded holes of the attachment plates 252.

A hard stop plate 258 protects the potentiometer 222 by preventing the potentiometer 222 from turning past its rotational maximum. The hard stop plate 258 does this by forming two angled faces 260 and 262 that form an angle above 90 degrees. The motion of the potentiometer 222 is limited by a hard stop screw 264 which contacts the angled faces 260 and 262 of the hard stop plate 258, preventing the potentiometer 222 from moving past a 270-degree range of motion. When the hard stop screw 264 is screwed into a hard stop hole 266, the hard stop screw 264 moves with the steering column 220. If the steering column 220 turns too far, the hard stop screw 264 contacts the hard stop plate 258. The hard stop plate 258 is held in place by two sets of screws 268 and 270, which go into two sets of threaded holes 272 and 274 in the hard stop plate 258. One set of holes 272 is comparatively shallow, to prevent one set of screws 268 from interfering with the hard stop plate 258 functioning. The other set of holes 274 is comparatively deep to provide additional structural integrity, in light of the fact that the first set of holes 272 are comparatively shallow. The other set of screws 270 going into the other set of holes 274 are longer than the first set of screws 268.

Figure 3A:
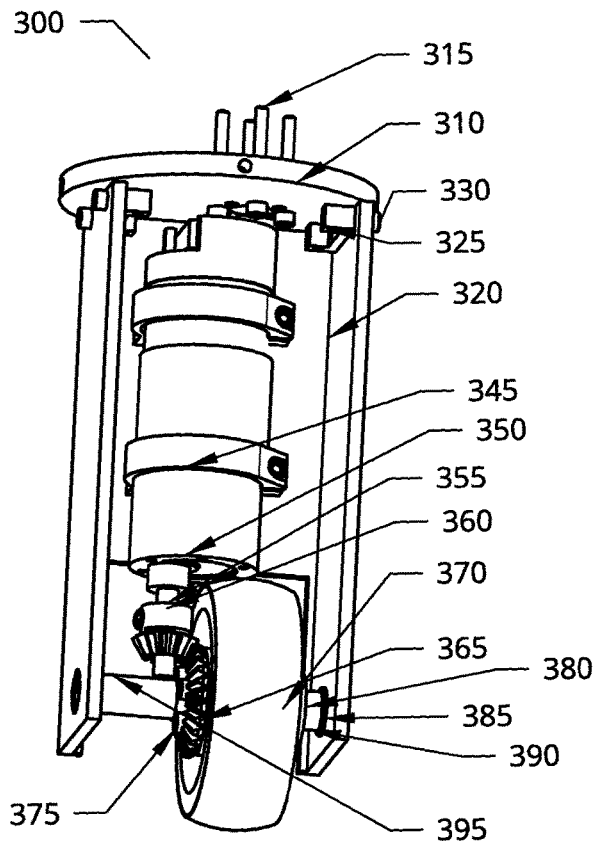
FIGS. 3a and 3b show perspective views of a swerve-drive unit in accordance with at least one embodiment of the present disclosure.
Figure 3B:
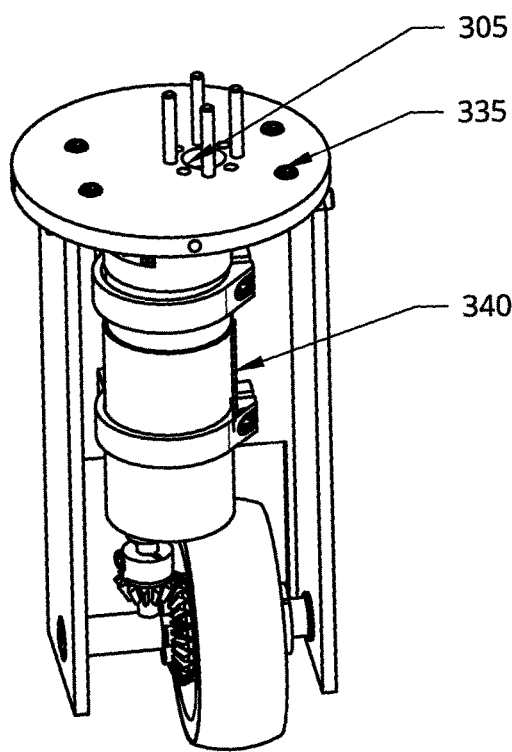

FIGS. 3a and 3b show perspective views of the drive section 300 of a swerve-drive unit 110 in accordance with at least one embodiment of the present disclosure. The shoulder 246 fits into the top hole 305 of the drive section 300 to ensure that the drive section 300 does not twist away from the steering section 200 and to maintain alignment of the through hole 242 of the steering column 220 with the top hole 305 of the drive section 300. The through hole 242 allows wires to pass from down below in the drive section 300 of the swerve-drive unit 110 up into the steering section 200 of the swerve-drive unit 110.

The top hole 305 is located in a top plate 310 of the drive section 300. The top plate 310 is secured to the steering column 220 by cap screws 315. The top plate 310 is attached to a case 320 using two dual-sided mounts 325 in the top corners of the closed side of the case 320. The dual-sided mounts 325 fit snugly against the inside edge of the case 320 and the top plate 310. The dual-sided mounts 325 are secured using two sets of screws 330 and 335. The first set of screws 330 pass horizontally through the case 320 into the dual-sided mounts 325. The second set of screws 335 pass vertically through the top plate 310 into the dual-sided mounts 325.

The case 320 houses a gear motor 340. The gear motor 340 is attached to the case 320 using two clamping mounts 345. The bottom end of the gear motor 340 is called a gear box 350. A shaft 355 protrudes from the gear box 350. A bevel gear 360 is mounted on the shaft 355. The bevel gear 360 is positioned on the shaft 355 such that the bevel gear 360 interlocks with another bevel gear 365 mounted to a wheel 370. The bevel gear 365 is secured to the wheel 370 by screws 375 through the bevel gear 365, wheel 370, and a hub 380. A stainless-steel d-shaft 385 passes through the bevel gear 365, wheel 370, and hub 380, connecting them with the case 320. The stainless-steel d-shaft 385 is secured into holes in the case 320 by a set of ball bearings 390. Two spacers 395 fit around the stainless-steel d-shaft 385 abutting the bevel gear 365 on one side and the hub 380 on the other side, giving the wheel 375 space to rotate without hitting the case 320.

Robot 100 has four wheels 370, but only one is pictured in FIG. 3. Each wheel 370 may be rotated independently of the other wheels 370. Thus, the collection of wheels 370 may spin in forward and reverse directions in any combination. For example, if the steering sections of all four swerve-drive units 110s are aligned and all wheels 370 rotate in a forward direction, the robot 100 moves in a forward direction, whereas if all wheels 370 rotate in a reverse direction, the robot 100 moves in a reverse direction. Additionally, the robot 100 is able to execute a turn by having each wheel 370 turn up to 45 degrees relative to the robot 100. This allows the wheels 370 to simultaneously turn and rotate.

Figures 4A, 4B:
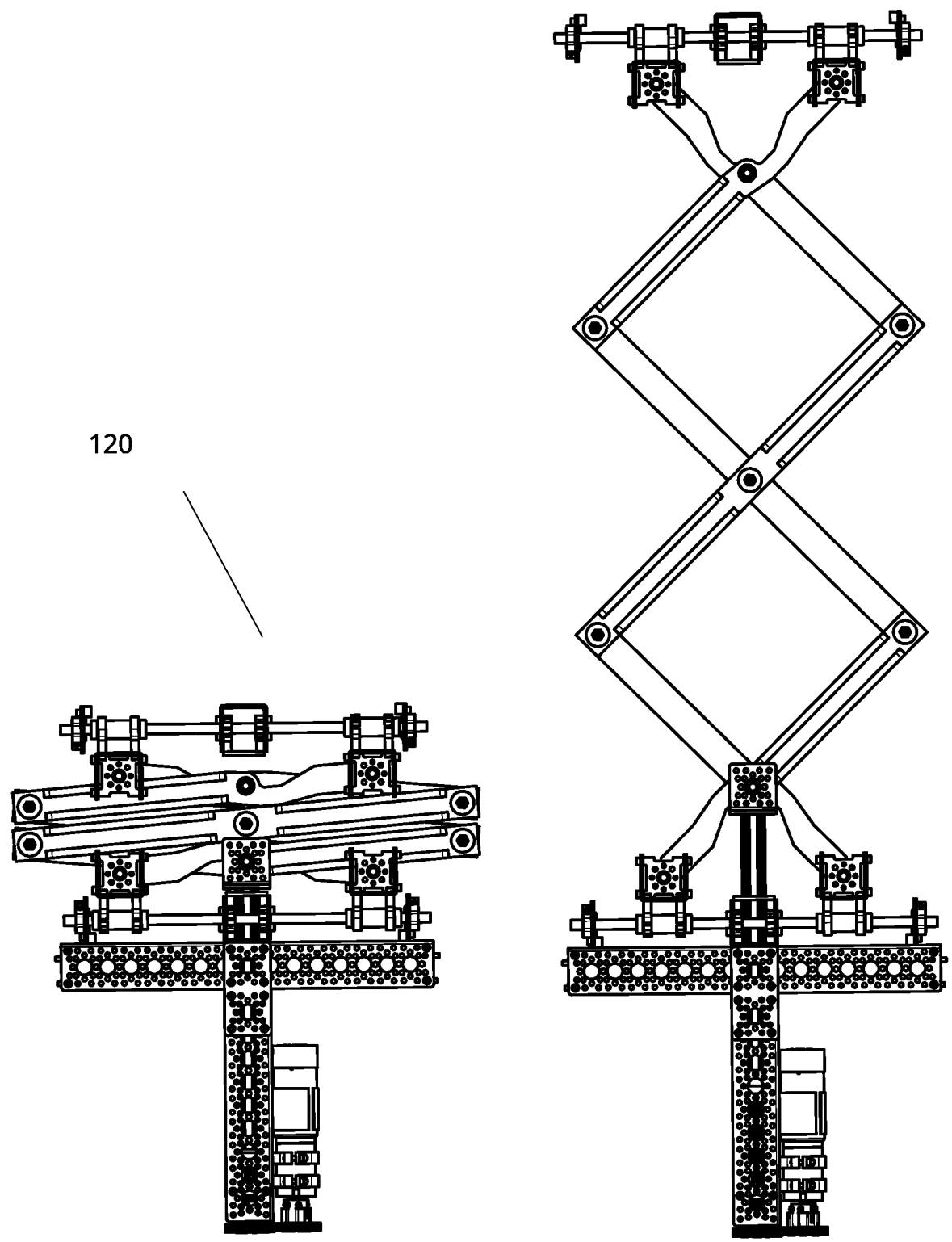
FIG. 4a, FIG. 4b, and FIG. 4c show perspective views of a scissor lift in accordance with at least one embodiment of the present disclosure.
Figure 4C:
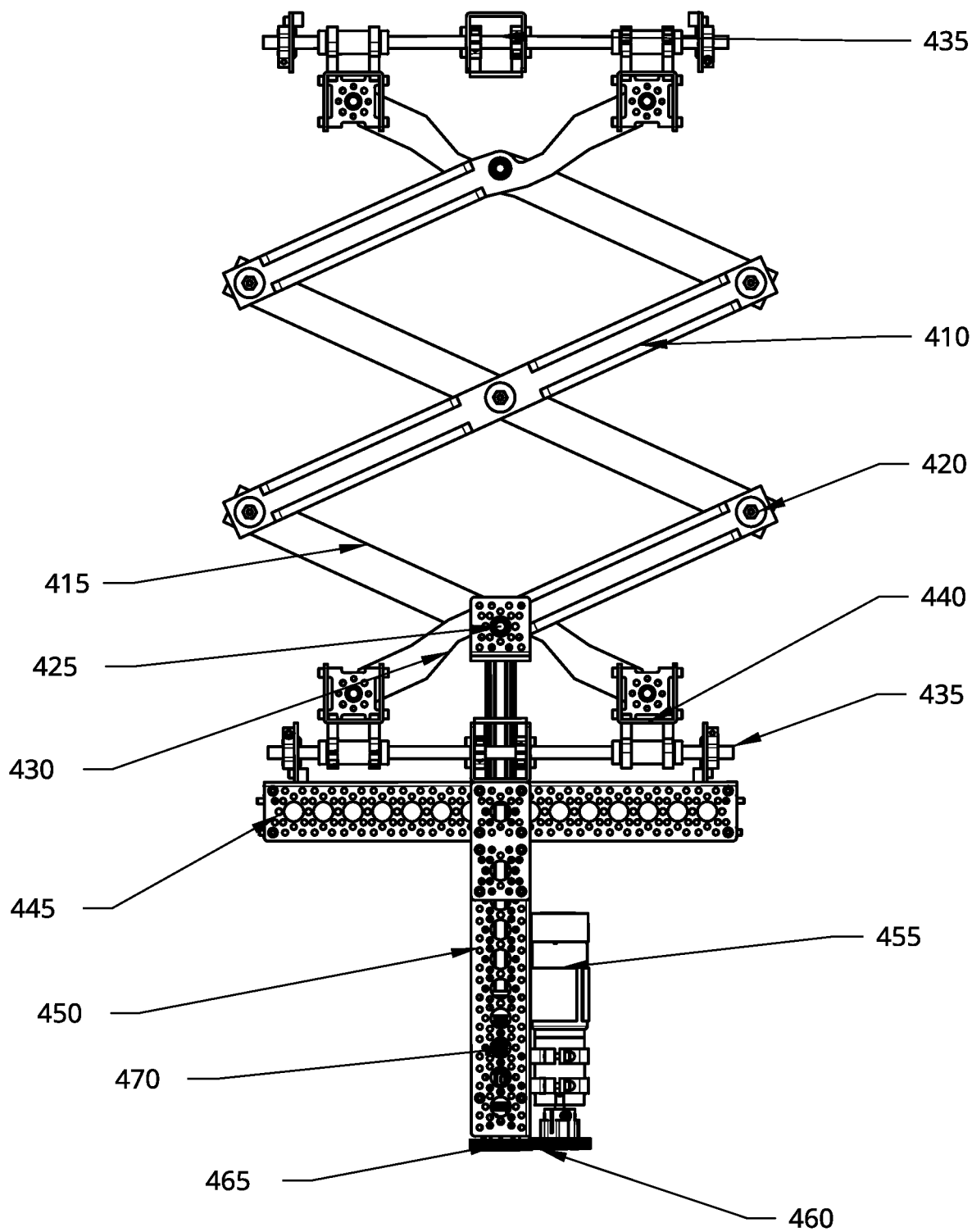

FIG. 4a, FIG. 4b, and FIG. 4c show perspective views of the scissor lift 120 in accordance with at least one embodiment of the present disclosure. In FIG. 4a, the scissor lift 120 is in the contracted position. In FIG. 4b, the scissor lift 120 is partially extended upward. In FIG. 4c, the scissor lift is in the extended position.

The scissor lift 120 includes bars 410 and 415 connected by joints 420 and 425. The top and bottom sets of bars 415 have indentations 430 to prevent the scissor lift 120 from colliding with sliding mechanisms 435. Joint 425 is the bottom joint that connects the bottom set of bars 415. The scissor lift 120 is considered asymmetrical because the bottom and top sets of bars 415 are shorter than the other sets of bars 410.

The scissor lift is anchored in place by a carriage 440 attached to the bottom sliding mechanism 435, which is attached to a bar 445. A bar 450 is attached to the middle of bar 445 such that bar 450 is perpendicular to bar 445, and the end of bar 450 is flush with bar 445. Bar 450 houses a portion of a piston mechanism 600. A top plate 190 may be attached to the top sliding mechanism 435. The scissor lift 120 can accommodate components attached to the top plate 190, which are raised and lowered with the movement of the scissor lift 120. Components may include decontamination box 130, crane 1100, or other attachments.

Extension of the scissor lift 120 is controlled by a motor 455, which rotates gears 460 and 465. Motor 455 and gears 460 and 465 are part of the piston mechanism 600. Gear 460 interlocks edges with gear 465 such that when gear 460 is rotated, gear 465 is also rotated. Gear 465 rotates a screw 470, causing screw 470 to move upwards linearly. Screw 470 is part of the piston mechanism 600. The top end of screw 470 is attached to joint 425. When the scissor lift is fully contracted, there is a slight separation in bars 410 and 415 due to their thickness. As screw 470 moves upward, it pushes joint 425 upward, further separating bars 410 and 415, extending the scissor lift 120.

Alternatively, if there is no initial separation in bars 410 and 415, the piston mechanism 600 is located in the central area of the robot 100, and the initial separation may be achieved by the piston mechanism 600 pushing on a box that lifts the top plate 190 up until there is initial separation in bars 410 and 415. For example, the top plate 190 may be pushed up three inches. Once there is initial separation in bars 410 and 415, the bars 410 and 415 may be further separated by a tube attached to the piston mechanism 600 such that the tube is perpendicular to the piston mechanism 600 and pushes up on joint 425. The scissor lift 120 may also alternatively raise at an upward angle such that the further the scissor lift 120 extends, the more to one side it moves. This can be achieved by anchoring one carriage 440 on the bottom sliding mechanism 435 and allowing the other carriage 440 of the bottom sliding mechanism 435 to be free moving, while anchoring the opposite side carriage 440 on the top sliding mechanism 435 and allowing the other side carriage 440 of the top sliding mechanism 435 to be free moving. The sets of bars 410 and 415 may alternatively be the same length.

Figure 5:
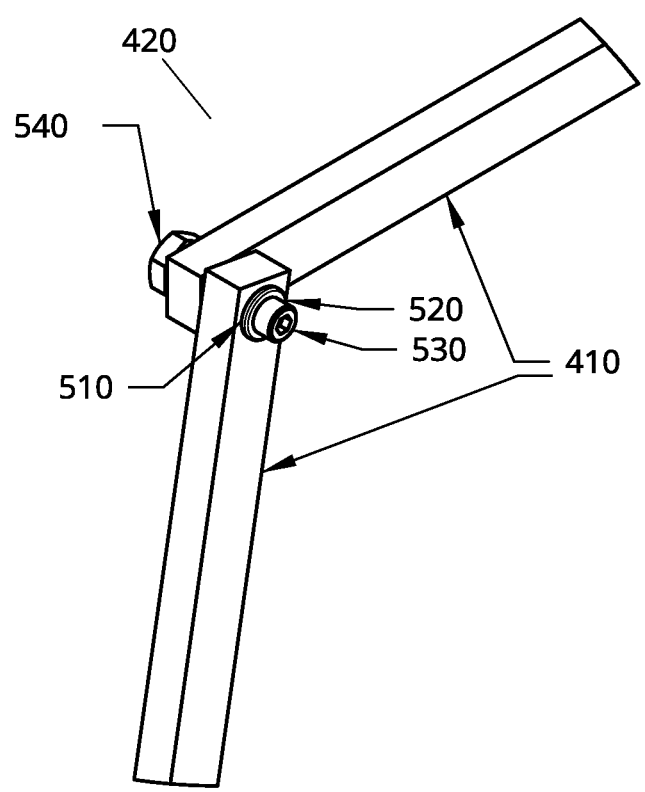
FIG. 5 shows a perspective view of a part of a scissor lift in accordance with at least one embodiment of the present disclosure.

FIG. 5 shows a perspective view of one of the joints 420 in the scissor lift 120 in accordance with at least one embodiment of the present disclosure. Joint 420 connects two bars 410 such that the bars 410 are able to rotate about joint 420 without significant friction.

Joint 420 includes a bushing 510 that extends through both bars 410. The bushing 510 should be short enough that the bars 410 do not have excess room to move apart and long enough that a set of crush washers 520, which abut the bushing 510 on either side, do not compress the bars 410. The crush washers 520 should only compress the bushing 510. Joint 420 includes a screw 530, which fits through the crush washers 520 and bushing 510. Screw 530 is secured on the end by a nut 540.

FIG. 6a and FIG. 6b show the piston mechanism 600 in accordance with at least one embodiment of the present disclosure. In FIG. 6a, a front view of the piston mechanism 600 is shown. In FIG. 6b, a perspective view of the piston mechanism 600 is shown.

The piston mechanism 600 includes motor 455, which rotates gears 460 and 465. Gear 460 interlocks edges with gear 465 such that when gear 460 is rotated, gear 465 is also rotated. Gear 465 rotates a screw 470, causing a screw nut that is secured to the bottom of an open x-rail 645 to move upwards linearly along with the open x-rail 645.

Gear 460 is attached to motor 455 using a clamping hub 605. Gear 465 is attached to screw 470 using a clamping hub 615. Clamping hubs 605 and 615 are secured by socket head cap screws 620 and 625. A carriage 630 sits between two washers 635 and 640 on the screw 470. Washer 635 abuts clamping hub 615 from above. Washer 640 abuts an open x-rail 645 from below. Open x-rail 645 houses screw 470. A hub spacer 680 abuts the open x-rail 645 from above. A ball bearing 685 is located inside the hub spacer 680 such that the top end of the ball bearing 685 protrudes from the hub spacer 680. A clamping collar 690 abuts the top of the ball bearing 685 from above. The clamping collar 690 is secured by a set screw 695. Screw 470 extends up beyond clamping collar 690 and down beyond gear 465.

Open x-rail 645 is attached to motor 455 using two T brackets 650 and 655. The T brackets 650 and 655 abut two spacers 660 and 665. The two spacers are attached to two clamping mounts 670 and 675, which are on motor 455. Two screws 680 and 685 secure the connection by passing through the T brackets 650 and 655, the spacers 660 and 665, and the clamping mounts 670 and 675.

The linear actuator is powered by motor 455, which turns the gear 460 that drives the main gear 465. The first gear is screwed to the motor by a motor hub 605, the same applies for the driven gear. The gear 465 turns a lead screw 470 which provides linear motion to a lead nut that travels up and down the actuator. The whole system is encased in an open x-rail 645. To increase the efficiency, the screw moves through bearings 630, 635, and 640. This reduces friction and acts as a spacer in between parts. The motor 455 is attached by two mounts 670 and 675.

Figure 7A:
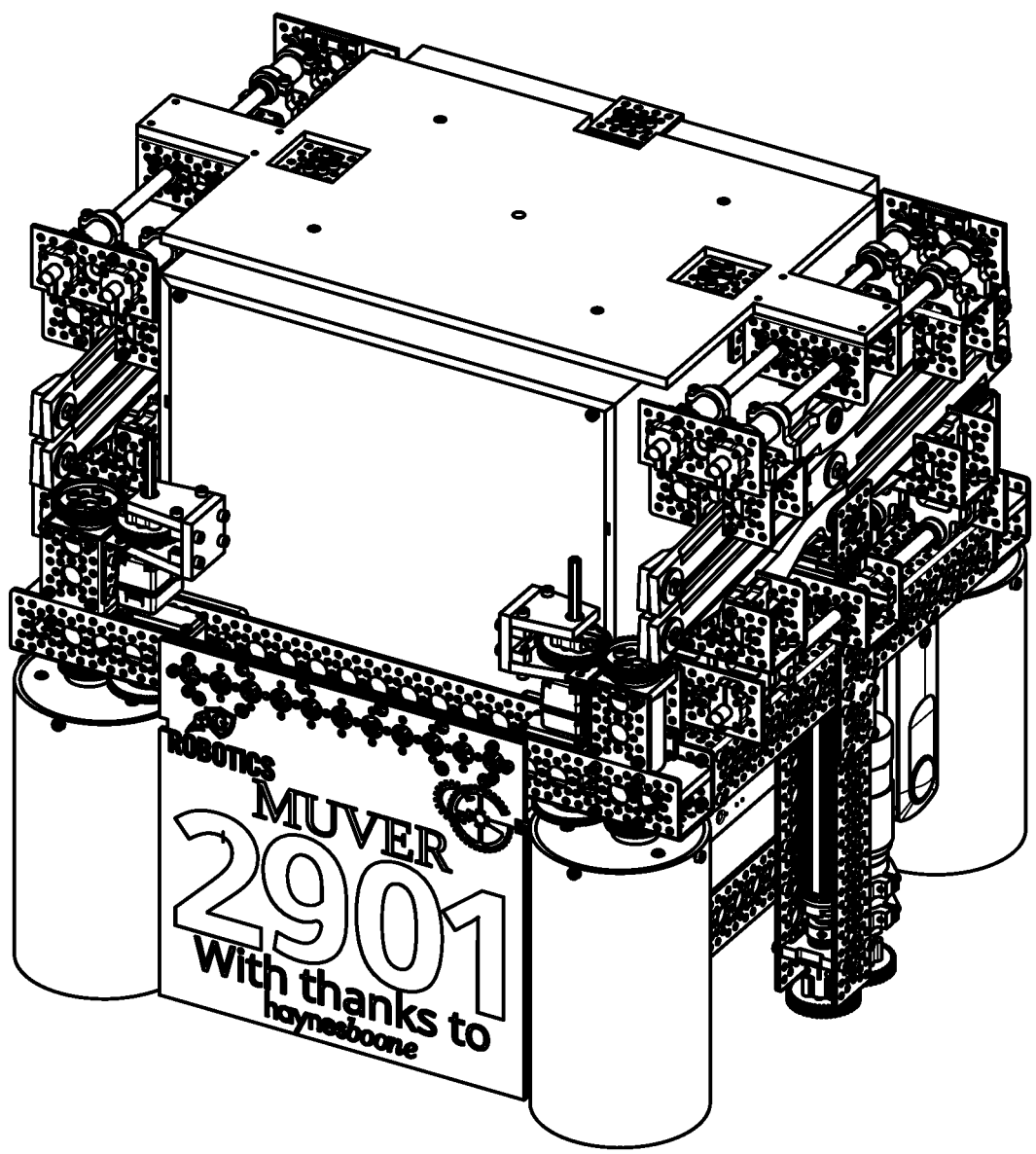
FIG. 7a, FIG. 7b, and FIG. 7c are front views of a decontamination box in multiple positions, in accordance with at least one embodiment of the present disclosure.
Figure 7B:
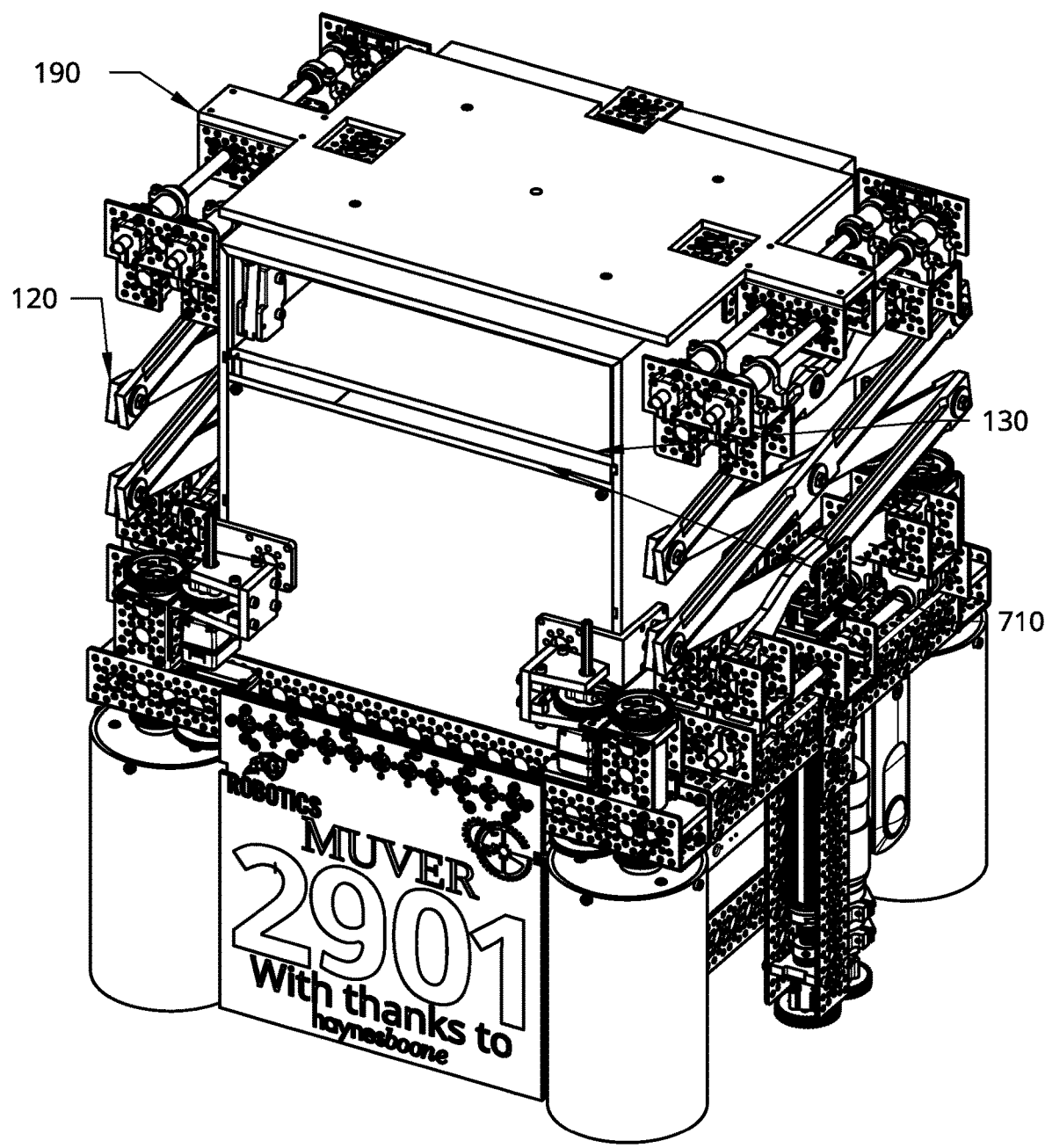
Figure 7C:
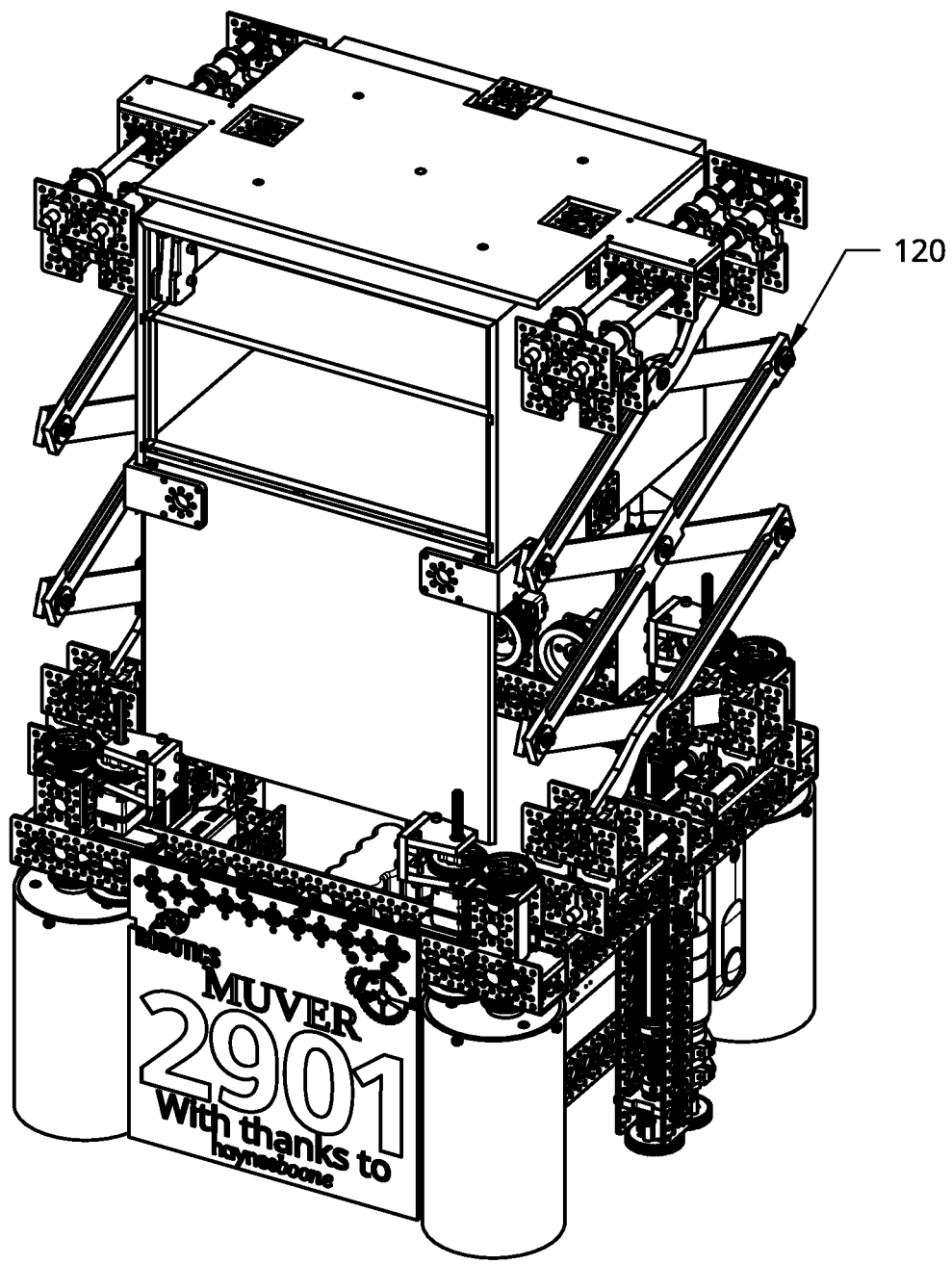

FIG. 7a, FIG. 7b, and FIG. 7c are front views of the process by which the decontamination box 130 moves to an open or closed position (e.g., to accept an item for decontamination or return an item after decontamination), in accordance with at least one embodiment of the present disclosure. In FIG. 7a, the decontamination box 130 is in the closed position. In FIG. 7b, the decontamination box 130 is partially opened. In FIG. 7c, the decontamination box 130 is in the open position.

The decontamination box 130 raises as the scissor lift 120 extends upward. The door 710 remains fixed in place as the decontamination box 130 raises with the scissor lift 120, revealing an opening in the decontamination box 130. When the scissor lift 120 is fully extended and the door 710 is not covering the opening in the decontamination box 130, the decontamination box 130 is in the open position and may accept an item for decontamination. When the scissor lift 120 is fully contracted and the door 710 covers the opening in the decontamination box 130, the decontamination box 130 is in the closed position. While the decontamination box 130 is in the closed position, a microswitch is activated that triggers decontamination inside the decontamination box 130. Decontamination may take three minutes. The decontamination box 130 may be instructed to raise or lower by, for example, using a smart phone with an application that sends a command to the robot 100 or using the camera 170 affixed to the robot 100 to scan a QR code. The decontamination box 130 may be instructed to decontaminate by, for example, using a smart phone with an application that sends a command to the robot 100. Once decontamination is completed, the decontamination box 130 raises to the open position again. Decontamination can occur while the robot 100 is driving to a new location to facilitate delivery of a decontaminated item.

Figure 8A:
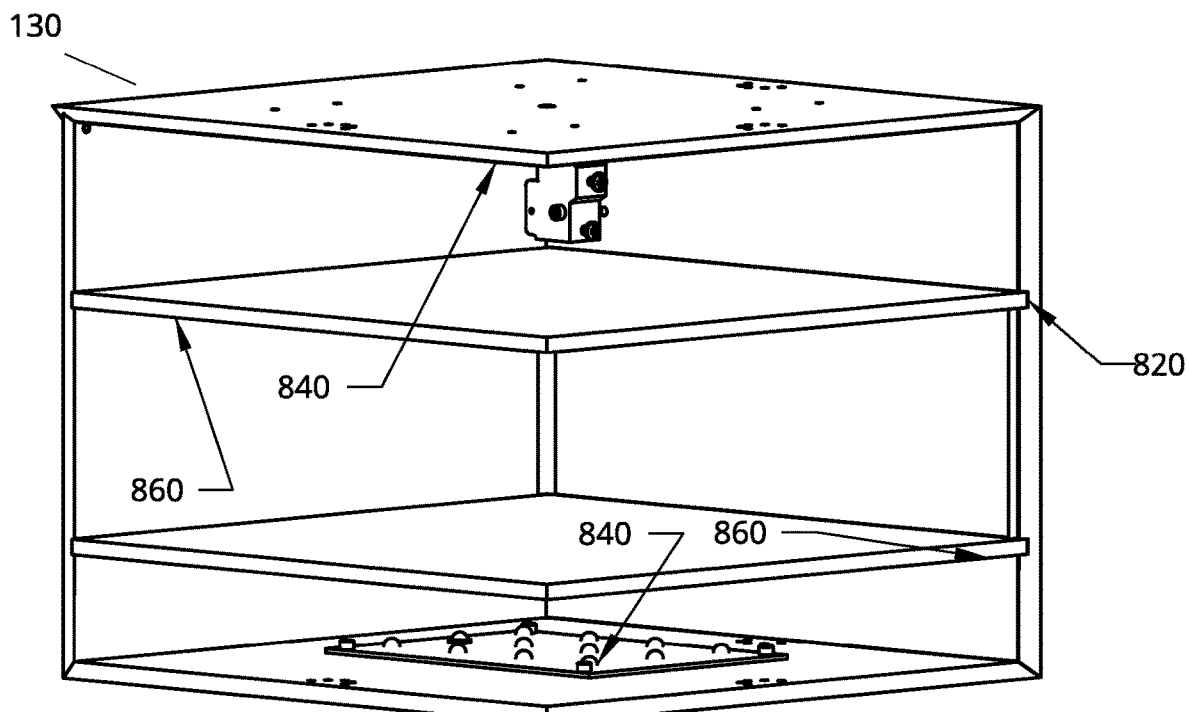
FIG. 8a and FIG. 8b show interior views of a decontamination box in accordance with at least one embodiment of the present disclosure.
Figure 8B:
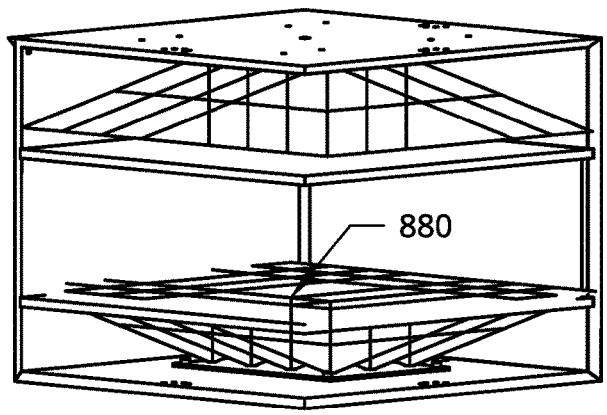

FIG. 8a and FIG. 8b show interior views of the decontamination box 130 in accordance with at least one embodiment of the present disclosure. FIG. 8a shows various components of the decontamination box 130. FIG. 8b shows the light coverage 880 of the decontamination box 130.

Glass plates 860 are installed in the interior of the decontamination box 130 for holding items undergoing decontamination. Two glass plates 860 are depicted in FIG. 8b, but greater or fewer glass plates 860 may be installed. The glass plates 860 may be borosilicate glass or other glass. The interior surfaces of decontamination box 130 may have a reflective coating 820. The reflective coating 820 preferably is highly reflective of ultraviolet wavelengths and may be a fluorinated polymer such as polytetrafluoroethylene, which is commercially available as Teflon. For example, the reflective coating 820 preferably reflects at least 90% of incident light in the 250-400 nm range, and even more preferably, reflects at least 95% of incident light in the 250-400 nm range. The reflective coating 820 may be a film affixed to the interior of the decontamination box 130 using glue and sealing the corners and edges with silicone caulking. A circuit board 840 with lights is affixed to the bottom interior of the decontamination box 130. Another circuit board 840 with lights is affixed to the top interior of the decontamination box 130. The lights may be ultraviolet LEDs equipped with suitable lensing to provide wide-angled light dispersion, such as a beam angle of about 120 degrees. There may be twelve LEDs per circuit board 840. The lights decontaminate items placed in the decontamination box 130. When turned on, the lights provide coverage 880 of the decontamination box 130. Preferably, the coverage 880 includes the entire interior of the decontamination box 130. Adjusting the number, spacing, and lensing of the lights may alter the coverage 880. The reflective coating 820 redirects unused light back onto the object being decontaminated.

Figures 9A, 9B:
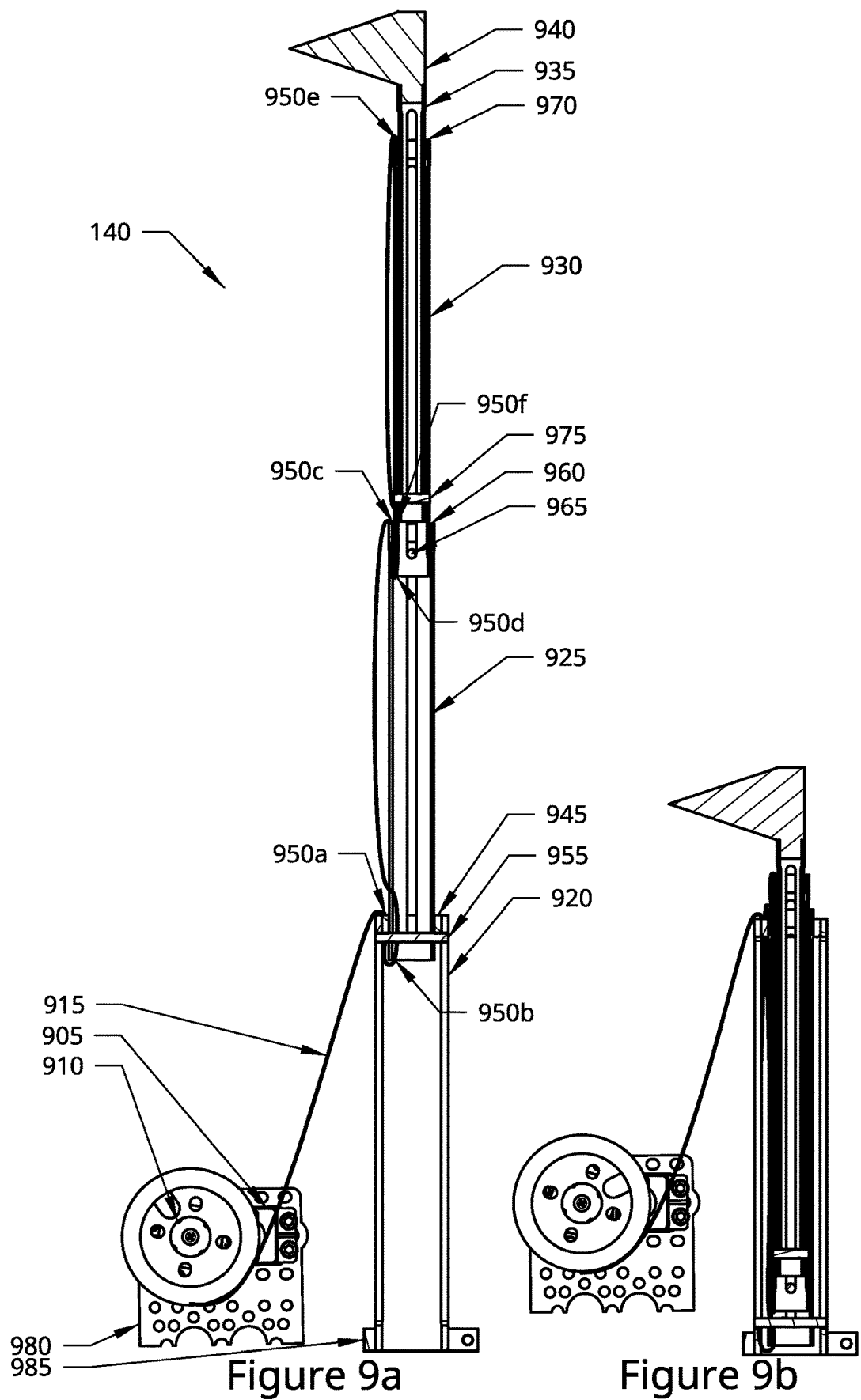
FIG. 9a and FIG. 9b show perspective views of a flag system in accordance with at least one embodiment of the present disclosure.

FIG. 9a and FIG. 9b show perspective views of the flag system 140 in accordance with at least one embodiment of the present disclosure. In FIG. 9a, the flag system 140 is depicted in its extended position. In FIG. 9b, the flag system 140 is depicted in its compacted position.

The flag system 140 is extended by using a winch servo 905, which rotates a pulley 910, to tighten and pull a string 915, which raises tubes 920, 925, 930, and 935. A flag cap 940 is attached to the top of tube 935.

The path of the string 915 through the flag system 140 is described. The string 915 passes through the top opening of tube 920 at point 950a, through a large acetal bushing 945, and around a pin 955. The string 915 next passes from the outside to the inside of tube 925 at the bottom opening of tube 925 at point 950b. The string 915 next passes through an opening in the side of tube 925 and passes along the outside to the top of tube 925 at point 950c. The string 915 next passes through the top opening of tube 925 and through a middle bushing 960. The string 915 next passes from the outside to the inside of tube 930 at the bottom opening of tube 930 at point 950d and passes around a pin 965. The string 915 next passes through an opening in the side of tube 930 and passes along the outside to the top of tube 930 at point 950e. The string 915 next passes through the top opening of tube 930 at point 950e, through an inner bushing 970, through the inside of tube 930, around an inner pin 975, and attaches to the bottom of tube 935 at point 950f.

The flag system 140 is attached to the robot 100 by a custom-cut servo mount 980 and a side-tapped clamping hub 985. The flag system 140 provides a visual notification to those nearby of the location or movement of the robot 100 using a flag cap 940, which is attached to and rests on the top of tube 935. The flag cap 940 may be 3D-printed and may include identifying information to identify the type of service provided by robot 100 (for example, an object decontamination service) or to identify the specific instance of robot 100 (for example, a serial number or other unique identifier).

Figure 10A:
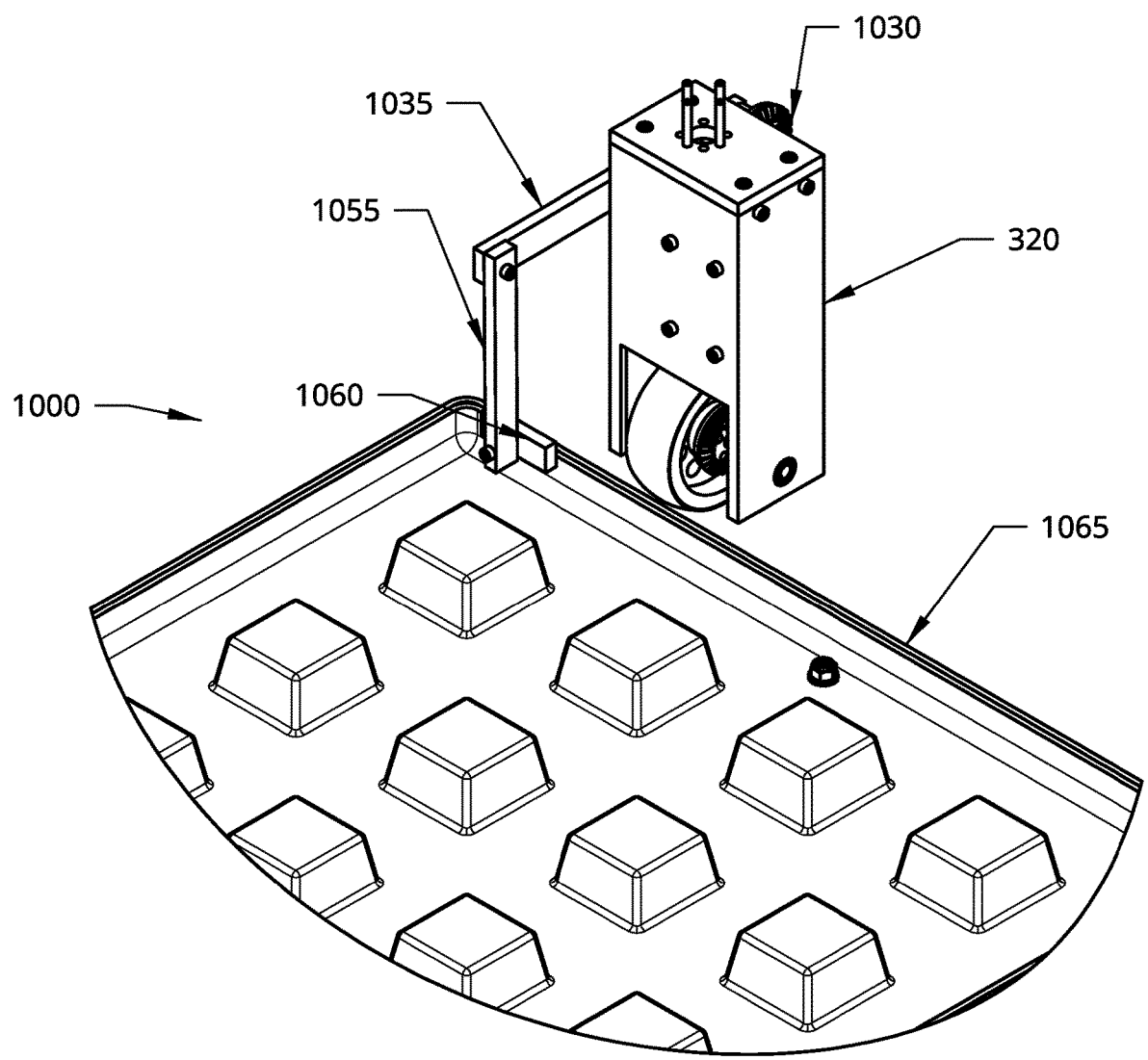
FIG. 10a, FIG. 10b, and FIG. 10c show a trailer dragging system in accordance with at least one embodiment of the present disclosure.
Figure 10B:
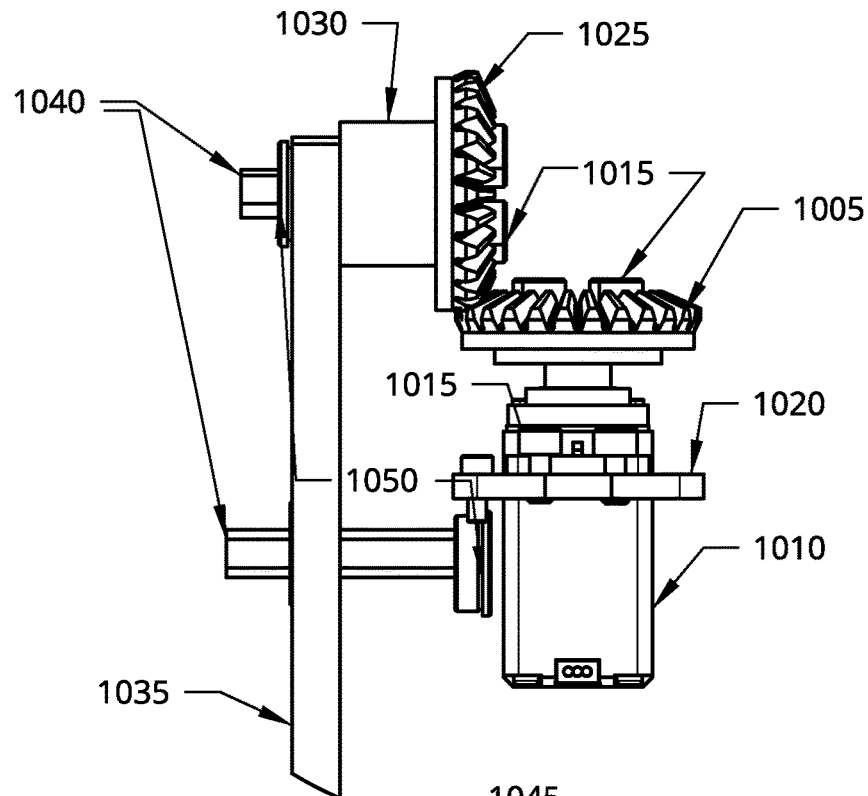
Figure 10C:
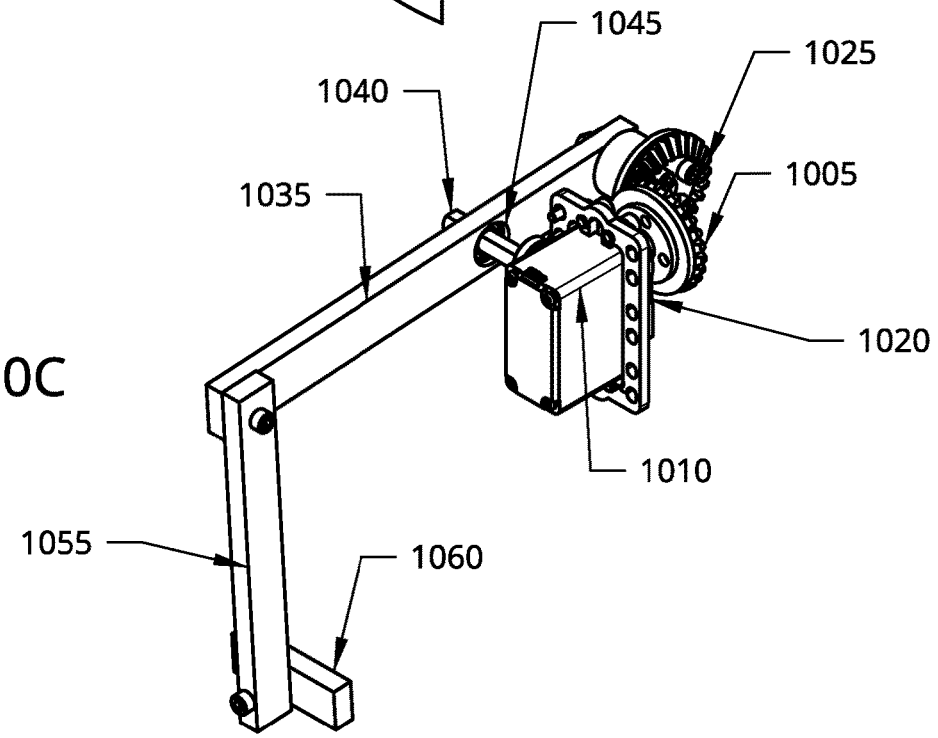

FIG. 10a, FIG. 10b, and FIG. 10c show the trailer dragging system 1000 in accordance with at least one embodiment of the present disclosure. In FIG. 10a, the trailer dragging system 1000 is depicted in a perspective view. In FIG. 10b, the trailer dragging system 1000 is depicted in a top view. In FIG. 10c, the trailer dragging system 1000 is depicted in a perspective view. As illustrated in FIG. 10a, an arm of the trailer dragging system 1000 may be deployed to engage with the lip of a plate 1065, thereby allowing the robot 100 to drag the plate 1065 to a new location as may be needed. The plate 1065 may be embossed with a waffle pattern, as shown, to facilitate the ordered arrangement or stacking of objects on the plate 1065.

The trailer dragging system 1000 includes a gear 1005 that is attached to a servo 1010 by screws 1015. The servo 1010 is attached to a case 320 using a servo mount 1020. The case 320 houses wheel 375. Gear 1005 interlocks edges with a gear 1025 such that when gear 1005 is rotated, gear 1025 is also rotated. Gear 1025 is attached to a spacer 1030 by screws 1015.

A bar 1035 is attached to the case 320 and spacer 1030 using stainless steel d-shafts 1040. Spacer 1030 fits snugly against bar 1035. Bar 1035 has two holes 1045, into which bearings 1050 are placed. The case 320 also has a hole 1045, into which a bearing 1050 is placed. All holes 1045 and bearings 1050 have the same diameter. The stainless-steel d-shafts 1040 fit inside the bearings 1050, connecting bar 1035 with the case 320 and spacer 1030.

Bar 1035 is the longest bar in the trailer dragging system 1000. One end of bar 1035 is connected in the manner discussed above to spacer 1030. The other end of bar 1035 extends past the case 320 surrounding the wheel 375 and attaches to one end of a bar 1055. Bar 1055 is attached such that bar 1055 is perpendicular to bar 1035 and does not extend down as far as the bottom of the case 320. The other end of bar 1055 attaches to a bar 1060 such that bar 1060 is perpendicular to, and flush with the end of, bar 1055.

Figure 11A:
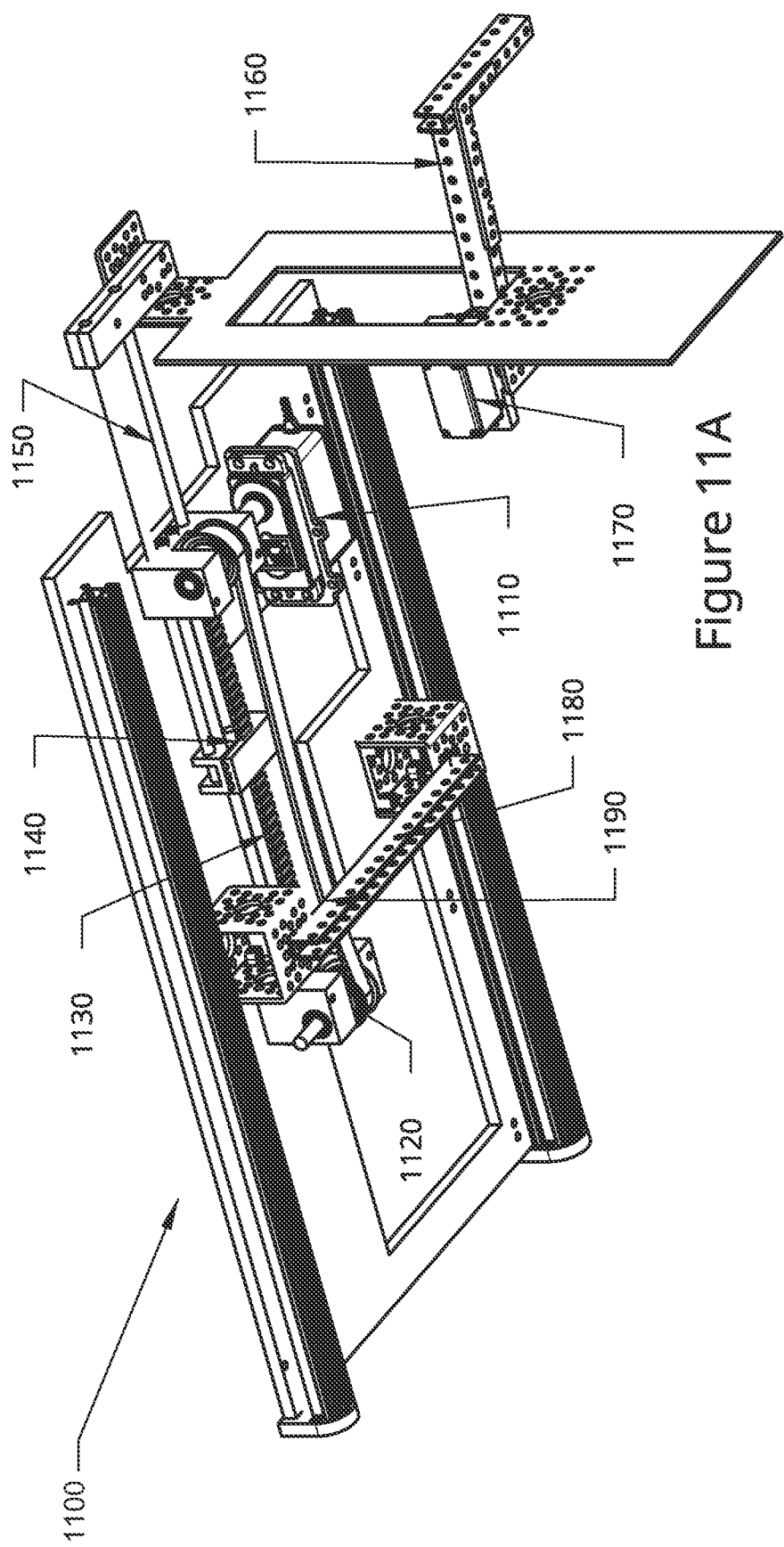
FIG. 11a and FIG. 11b show perspective views of a crane in accordance with at least one embodiment of the present disclosure.
Figure 11B:
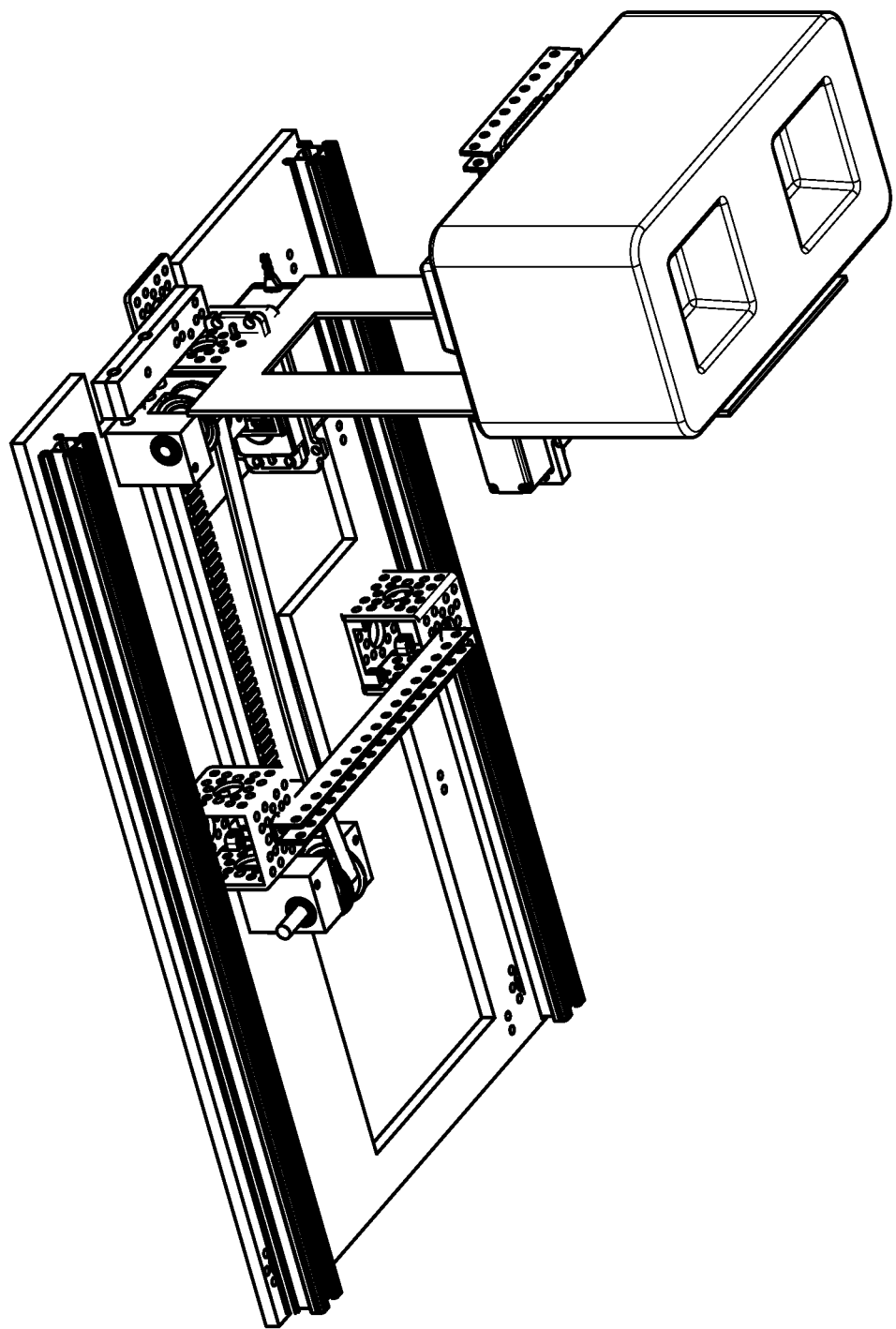

FIG. 11a and FIG. 11b show perspective views of a crane 1100 in accordance with at least one embodiment of the present disclosure. In FIG. 11a, the crane 1100 is in its extended position. In FIG. 11b, the crane 1100 is in its retracted position.

The crane 1100 may be mounted to the top plate 190, either in place of or in addition to decontamination box 130. Extension of the crane is controlled by a servo 1110, which rotates pinion pulleys 1120 to turn a belt 1130. A slider 1140 is attached to the belt 1130. Slider 1140 is attached to tubes 1150, which form the arm of the crane 1100. As the belt 1130 turns, the slider pushes the tubes 1150 out, extending the arm of the crane 1100. Tubes 1150 may be carbon fiber rods to decrease the weight of the crane 1100 to allow the robot 100 to lift the crane 1100. A bar 1180 stretches across the crane 1100 and makes contact with the belt 1130 at point 1190 to prevent the crane 1100 from interfering with the rest of the robot 100. Servo 1110 is able to track relative position of the crane 1100. Servo 1110 may be a winch servo. Servo 1110 may complete eight full turns, each turn achieving a 360-degree rotation. The eight turns of the servo 1110 rotate the belt 1130 less than one full turn. The crane 1100 may include a claw 1160 for grabbing items. Contraction of the claw 1160 is controlled by a servo 1170. Alternatively, the crane 1100 may include any other attachment.

Figure 12:
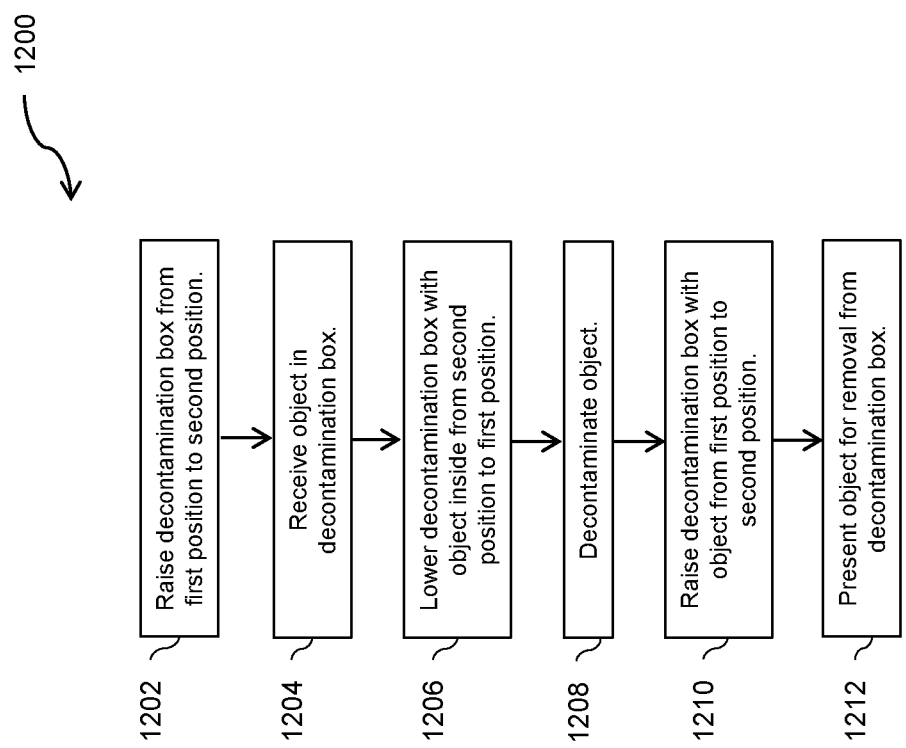
FIG. 12 shows a decontamination method in accordance with at least one embodiment of the present disclosure.

FIG. 12 shows a method of decontamination in accordance with at least one embodiment of the present disclosure. In step 1202, the robot 100 raises the decontamination box 130 from a first position to a second position. The first position may be when the decontamination box 130 is in a closed position. The second position may be when the decontamination box 130 is in an open position. The scissor lift 120 may be responsible for raising the decontamination box 130. In step 1204, the decontamination box 130 receives an object for decontamination. The object may be a piece of medical equipment, such as PPE. The object may be placed on one of the glass plates 860 in the decontamination box 130.

In step 1206, the robot 100 lowers the decontamination box 130 from the second position to the first position. The scissor lift 120 may be responsible for lowering the decontamination box 130. The decontamination box 130 may be instructed to lower by, for example, using a smart phone with an application that sends a command to the robot 100 or using the camera 170 affixed to the robot 100 to scan a QR code. In step 1208, the decontamination box 130 decontaminates the object. Decontamination may be triggered by a microswitch, which is activated when the decontamination box 130 is in the closed position. Decontamination may take three minutes. Decontamination may occur while the robot 100 is driving to a new location to facilitate delivery of the decontaminated object. During decontamination, the object may be irradiated with ultraviolet LED light from at least two different directions. Unused light may be redirected back onto the object due to a reflective coating 820 on the interior surfaces of the decontamination box 130. In step 1210, the robot 100 raises the decontamination box 130 with the decontaminated object from the first position to the second position.

Based on design considerations and depending on the implementation, the robot can be made from a variety of different materials and structural elements and can comprise a variety of different structural arrangements that perform the same functions. As will be readily appreciated by those having ordinary skill in the art after becoming familiar with the teachings herein, the robot can be autonomous, semi-autonomous, or teleoperated. Accordingly, it can be seen that decontamination robot 100 with swerve drive and scissor lift fills a long-standing need in the art, by providing a robot that is capable of moving around on a work surface (e.g., a floor or ground surface), retrieving target objects from the work surface, moving the target objects, depositing the target objects in another location, receiving target objects for decontamination, decontaminating the target objects, moving the target objects while decontaminating, and supplying the decontaminated target objects to the same or another location.

The robot of the present disclosure may include one or more processors or controllers comprising any combination of general-purpose computing devices, reduced instruction set computing (RISC) devices, application-specific integrated circuits (ASICs), field programmable gate arrays (FPGAs), or other related logic devices, including mechanical and quantum computers. In some embodiments, the processor comprises a memory in which instructions or information are stored, and the processor operates based on the instructions or information. The memory may be co-located on the same board or chip with processing elements or else located external to a board or chip containing processing elements. The memory may comprise any combination of read-only memory (ROM), programmable read-only memory (PROM), electrically erasable read-only memory (EEPROM), magnetic or electronic random access memory (RAM), flash memory, disk or tape drive, or other related memory types.

External communication between the robot and an operator, base station, ground station, or cloud server (including but not limited to software updates, firmware updates, or data downloads from the robot) may be accomplished using any suitable wireless or wired communication technology, such as a cable interface such as a USB, micro USB, Lightning, or FireWire interface, Bluetooth, Wi-Fi, ZigBee, Li-Fi, or cellular data connections such as 2G/GSM, 3G/UMTS, 4G/LTE/WiMax, or 5G. For example, a Bluetooth Low Energy (BLE) radio can be used to establish connectivity with a cloud service, for transmission of data, and for receipt of software patches. The controller may be configured to communicate with a remote server, or a local device such as a laptop, tablet, or handheld device, or may include a display capable of showing status variables and other information.

Communication, if any, within or between the components of the robot may be through numerous methods or protocols. Serial communication protocols may include but are not limited to SPI, I²C, RS-232, RS-485, CAN, Ethernet, ARINC 429, MODBUS, MIL-STD-1553, or any other suitable method or protocol. Parallel protocols including but not limited to ISA, ATA, SCSI, PCI, IEEE-488, IEEE-1284, and other suitable protocols. Where appropriate, serial and parallel communications may be bridged by a UART, USART, SERDES, or other appropriate subsystem.

A number of variations are possible on the examples and embodiments described above. The technology described herein may be employed in mining, space exploration, and hospitals or other medical environments.

Accordingly, the logical operations making up the embodiments of the technology described herein are referred to variously as operations, steps, objects, elements, components, or modules. Furthermore, it should be understood that these may occur in any order, unless explicitly claimed otherwise or a specific order is inherently necessitated by the claim language.

All directional references e.g., upper, lower, inner, outer, upward, downward, left, right, lateral, front, back, top, bottom, above, below, vertical, horizontal, clockwise, counterclockwise, proximal, and distal are only used for identification purposes to aid the reader's understanding of the claimed subject matter, and do not create limitations, particularly as to the position, orientation, or use of the decontamination robot with swerve drive and scissor lift. Connection references, e.g., attached, coupled, connected, and joined are to be construed broadly and may include intermediate members between a collection of elements and relative movement between elements unless otherwise indicated. As such, connection references do not necessarily imply that two elements are directly connected and in fixed relation to each other. The term "or" shall be interpreted to mean "and/or" rather than "exclusive or." Unless otherwise noted in the claims, stated values shall be interpreted as illustrative only and shall not be taken to be limiting.

The above specification, examples and data provide a complete description of the structure and use of exemplary embodiments of the decontamination robot with swerve drive and scissor lift as defined in the claims. Although various embodiments of the claimed subject matter have been described above with a certain degree of particularity, or with reference to one or more individual embodiments, those skilled in the art could make numerous alterations to the disclosed embodiments without departing from the spirit or scope of the claimed subject matter.

Still other embodiments are contemplated. It is intended that all matter contained in the above description and shown in the accompanying drawings shall be interpreted as illustrative only of particular embodiments and not limiting. Changes in detail or structure may be made without departing from the basic elements of the subject matter as defined in the following claims.

What is claimed is:

1. A decontamination robot, the robot comprising:
   a decontamination box including at least two arrays of ultraviolet LEDs, the two arrays arranged to irradiate an object placed inside the decontamination box from at least two independent directions, the decontamination box further including an interior surface providing at least 90% reflectivity of ultraviolet light;
   a drivetrain including a frame and four swerve-drive units connected by the frame, each swerve-drive unit including a wheel and capable of rotating the wheel on a first axis, where the four swerve-drive units are arranged such that the first axes of the four wheels are substantially coplanar and define a plane that is substantially parallel to a working surface, and where each swerve-drive unit is capable of rotating the wheel on a second axis, where the second axis is perpendicular to the plane;
   the drivetrain further including a processor to provide control signals to the four swerve-drive units to coordinate the rotation of the wheels about their first and second axes to generate translational motion of the decontamination robot on the working surface;
   a scissor lift capable of raising the decontamination box from a first position to a second position, wherein the scissor lift comprises a plurality of bars connected by a plurality of joints such that the plurality of bars form a series of crosses;
   a top plate attached to a top of the decontamination box;
   a flag configured to extend via a vertically telescoping shaft, calling attention to the decontamination robot;
   a crane mounted outside the decontamination box to an upper surface of the top plate; and
   a claw attached to the crane configured to selectively engage with one or more target objects above the working surface.

2. The decontamination robot of claim 1, wherein the decontamination box comprises:
 at least one plate that is substantially transparent to ultraviolet radiation and configured to hold an item for decontamination; and
 wherein each array of LED lights is mounted on a circuit board.

3. The decontamination robot of claim 1, wherein the scissor lift is connected to a bottom set of carriages attached to a bottom sliding mechanism and a top set of carriages attached to a top sliding mechanism, the bottom sliding mechanism being connected to a horizontal bar.

4. The decontamination robot of claim 1, further comprising a piston configured to exert upward force on the scissor lift such that the scissor lift extends.

5. The decontamination robot of claim 1, wherein each swerve-drive unit comprises:
 a steering unit configured to rotate the wheel about the second axis, wherein the steering unit comprises:
  a steering column;
  a potentiometer arranged to provide a signal corresponding to a rotational angle of the steering column;
  a servo configured to rotate the steering column; and
  a hard stop plate for protecting the potentiometer and the servo from over-rotation; and
 a drive unit configured to rotate the wheel about the first axis, wherein the drive unit comprises a gear motor configured to selectively rotate the wheel about the first axis in a clockwise and counterclockwise motion.

6. The decontamination robot of claim 1, further comprising at least one side plate attached to the frame of the drivetrain and extending down toward the floor such that the side plate covers a space between two of the swerve-drive units, the side plate configured to prevent debris from becoming trapped under the frame of the drivetrain, thereby protecting an undercarriage area of the decontamination robot from damage.

7. The decontamination robot of claim 1, further comprising a camera capable of scanning a QR code.

8. The decontamination robot of claim 1, wherein the processor is a smartphone.

9. The decontamination robot of claim 8, wherein the processor keeps track of an orientation of the decontamination robot by integrating an inertial measurement unit gyroscope, and wherein the processor keeps track of a position of the decontamination robot by integrating traction drivetrain rotation encoders, and wherein the processor detects a presence of a nearby object based on an input from a camera.

10. The decontamination robot of claim 1, further comprising a trailer dragger configured to selectively engage with a target object on the working surface.

* * * * *